United States Patent [19]
Christensen et al.

[11] Patent Number: 6,156,553
[45] Date of Patent: Dec. 5, 2000

[54] RECOMBINANT ENZYME WITH DEXTRANASE ACTIVITY

[75] Inventors: Tove Christensen, Lyngby; Claus Crone Fuglsang, Nivå; Torben Halkier, Birkerød; Charlotte Johansen, Holte, all of Denmark

[73] Assignee: Novo Nordisk A/S, Bagsvaerd, Denmark

[21] Appl. No.: 09/217,796

[22] Filed: Dec. 21, 1998

Related U.S. Application Data

[63] Continuation of application No. PCT/DK97/00284, Jun. 30, 1997.

[30] Foreign Application Priority Data

Jun. 28, 1996 [DK] Denmark ................................. 0714/96
Aug. 30, 1996 [DK] Denmark ................................. 0919/96

[51] Int. Cl.[7] .............................. C12N 9/46; C12N 1/20; C12N 15/00
[52] U.S. Cl. ..................... 435/211; 435/183; 435/206; 435/252.3; 435/254.1; 435/254.2; 435/254.3; 435/320.1
[58] Field of Search ...................... 435/183, 200, 435/203, 211, 243, 252.3, 254.1, 254.11, 254.3, 254.7, 256.1, 320.1, 262

[56] References Cited

FOREIGN PATENT DOCUMENTS 0 663 433 A1   7/1995   European Pat. Off. .

OTHER PUBLICATIONS

Le Gal–Coeffet et al. Expression in Apergillus niger of the starch binding domain of glucoamylase. European Journal of Biochemistry. vol. 233:561–567, 1995.

J.M. Lee et al. (1985) Enzyme Microb. Technol. 7:573–577.

Sun et al., Chem. Abstr. (Jun., 1989) Ann. NY Acad. Sci. pp. 192–194.

Xiulan et al., Chem. Abstr. Abstr. No. 179275u, pp. 334–339.

Galvez–Mariscal et al., (1991) Appl. Microbiol. Biotechnol. 36:327–331.

Jinwu et al., Chem. Abstr. Abstr. No. 218770w, 28 (1):45–55.

*Primary Examiner*—Ponnathapu Achutamurthy
*Assistant Examiner*—Manjunath Rao
*Attorney, Agent, or Firm*—Elias J. Lambiris; Valeta Gregg

[57] ABSTRACT

The present invention relates to a cloned DNA sequence encoding an enzyme with dextranase activity, a recombinant expression vector comprising said DNA sequence, a filamentous fungus host cell, a method for producing said recombinant dextranase, and the isolated and purified enzyme.

The invention also relates to compositions comprising the recombinant enzyme, oral care compositions and products and the use for removing of dental plaque.

12 Claims, 8 Drawing Sheets

RECOMBINANT ENZYME WITH DEXTRANASE ACTIVITY

CROSS-REFERENCE TO RELATED APPLICATIONS

This application is a continuation of PCT/DK97/00284 filed Jun. 30, 1997 and claims priority under 35 U.S.C. 119 of Danish applications 0714/96 filed Jun. 28, 1996 and 0919/96 filed Aug. 30, 1996, the contents of which are fully incorporated herein by reference

FIELD OF THE INVENTION

The present invention relates to a cloned DNA sequence encoding an enzyme with dextranase activity, a recombinant expression vector comprising said DNA sequence, a filamentous fungus host cell, a method for producing said recombinant dextranase, and the isolated and purified enzyme.

The invention also relates to compositions comprising the recombinant enzyme, oral care compositions and products and the use for removing of dental plaque.

BACKGROUND OF THE INVENTION

Dextranases are α-1,6-glucanases (E.C. 3.2.1.11), also known as 1,6-α-D-glucan 6-glucanohydrolases, which degrade the α-1,6-glycosidic linkages in dextran.

Dextranases are known to be useful for a number of applications including the use as ingredient in dentifrice for prevent dental caries, plaque and/or tartar and for hydrolysis of raw sugar juice or syrup of sugar canes and sugar beets.

Several micro-organisms are known to be capable of producing dextranases, among them fungi of the genera Penicillium, Paecilomyces, Aspergillus, Fusarium, Spicaria, Verticillium, Helminthosporium and Chaetomium; bacteria of the genera Lactobacillus, Streptococcus, Cellvibrio, Cytophaga, Brevibacterium, Pseudomonas, Corynebacterium, Arthrobacter and Flavobacterium, and yeasts such as *Lipomyces starkeyi*.

A commercially available dextranase, sold as an industrial enzyme for breaking down raw sugar juice, is Dextranase 50L from Novo Nordisk produced by fermentation of a strain of Paecilomyces sp.

Below are summarised prior art documents concerning dextranase and applications thereof.

Prior Art Documents

EP 663 443 (Centro de Ingenieria Genetica y Biotechnologia) describes a dextranase derived from *Penicillium miniotuteum*. The dextranase can be expressed heterologously in the yeast *Pichia pastoris*. Said recombinant enzyme has an optimum temperature in the range from 55° C. to 60° C., a N-glycosylation percentage between 13 and 15% and a half-life time of about 7.6 hours at 50° C.

SUMMARY OF THE INVENTION

Figure 1:
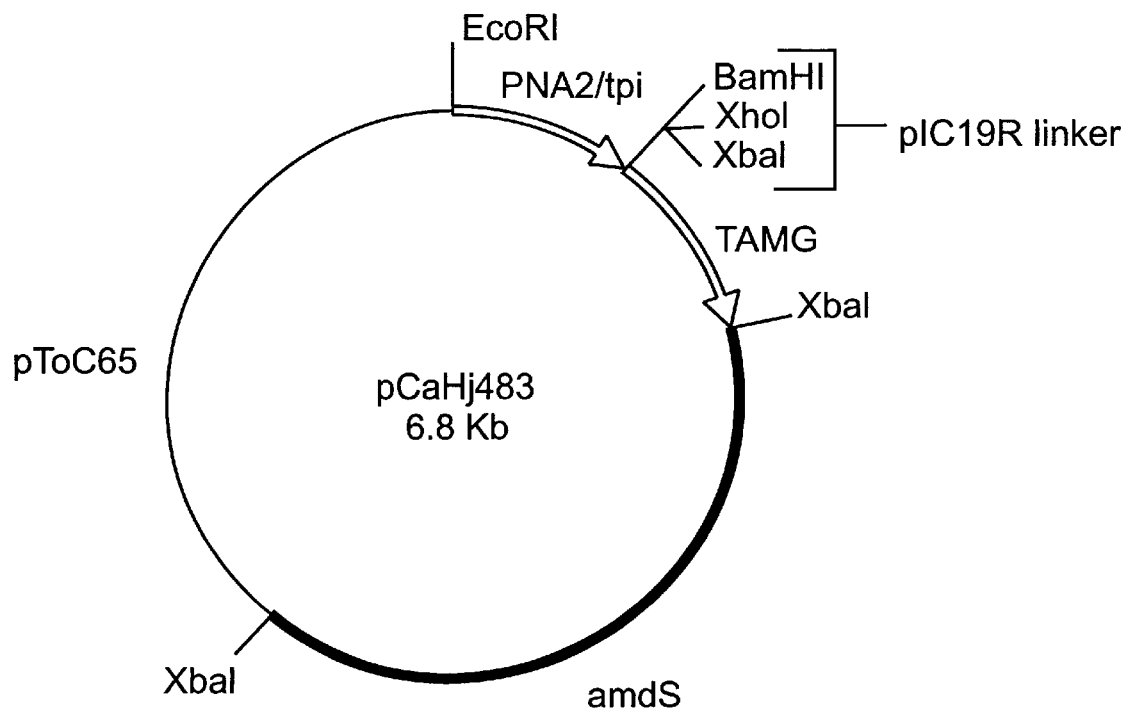
FIG. 1 shows plasmid pCaHj483

The object of the invention is to provide a recombinant dextranase from *Paecilomyces lilacinus* by heterologous production in a filamentous fungi host cell.

The present inventors have as the first cloned the complete DNA sequence encoding an enzyme with dextranase activity from *Paecilomyces lilacinus* and produced it heterologously in a filamentous fungi host cell. Said enzyme has previously only been produced homologously in *Paecilomyces lilacinus*. Consequently, according to prior art the enzyme product comprising said enzyme with dextranase activity is produced together with a mixture of other enzyme activities. It is advantageous to be able to produce a recombinant dextranase heterologously in a suitable host, as it is possible to provide a single component dextranase. Further, it facilitates providing an isolated and purified enzyme of the invention in industrial scale.

In the context of the present invention the term "heterologous" production means expression of a recombinant enzyme in a host organism different from the original donor organism.

The term "homologous" production means expression of the wild-type enzyme by the original organism.

The complete DNA sequence, shown in SEQ ID no. 1, encoding the dextranase of the invention, comprised in the plasmid pToc325, has been transformed into the bacteria strain *Escherichia coli* DH5α. The strain is deposited at DSM under the number DSM 10706. This will be described further below.

By a database alignment search it was found that the DNA sequence shown in SEQ ID no. 1 is novel. The highest degree of homology found was 59% to the above mentioned *Penicillium miniotuteum* (MUCL no. 38929) deposited on Aug. 22, 1994 under the provisions of the Budapest Treaty with the Mycotheque de l'Université Catholique de Louvain (MUCL). The DNA and amino acid sequences are disclosed in EP 0 663 443.

In the first aspect the invention relates to a DNA construct comprising a DNA sequence encoding an enzyme exhibiting dextranase activity, which DNA sequence comprises
  a) the dextranase encoding part of the DNA sequence shown in SEQ ID no. 1, and/or the DNA sequence obtainable from *E. coli* DSM 35 10706, or
  b) an analogue of the DNA sequence shown defined in a), which
    i) is at least 80% homologous with the DNA sequence shown in SEQ ID no. 1 and/or the DNA sequence obtainable from *E. coli* DSM 10706, or
    ii) hybridizes with the same oligonucleotide probe as the DNA sequence shown in SEQ ID no. 1 and/or the DNA sequence obtainable from *E. coli* DSM 10706, or
    iii) encodes a polypeptide which is 80% homologous with the polypeptide encoded by a DNA sequence comprising the DNA sequence shown in SEQ ID no.

1 and/or the DNA sequence obtainable from *E. coli* DSM 10706, or iv) encodes a polypeptide which is immunologically reactive with an antibody raised against a purified dextranase encoded by the DNA sequence shown in SEQ ID no. 1 derived from *Paecilomyces lilacinus* and/or obtainable from *E. coli,* DSM 10706.

In the present context, the "analogue" of the DNA sequence shown in SEQ ID no. 1 and/or the DNA sequence obtainable from *E. coli* DSM 10706, is intended to indicate any DNA sequence encoding an enzyme exhibiting dextranase activity, which has at least one of the properties i)–iv).

The analogous DNA sequence may be isolated from another or related (e.g. the same) organism producing the enzyme exhibiting dextranase activity on the basis of a partial sequence of the DNA sequences shown in SEQ ID no. 1 and/or obtainable from *E. coli,* DSM 10706, e.g. using the procedures described herein, and thus, e.g. be an allelic or species variant of the DNA sequence shown herein, may be constructed on the basis of any partial DNA sequence of the DNA sequence shown in SEQ ID no. 1, e.g. by introduction of nucleotide substitutions which do not give rise to another amino acid sequence of the dextranase encoded by the DNA sequence, but which correspond to the codon usage of the host organism intended for production of the enzyme, or by introduction of nucleotide substitutions which may give rise to a different amino acid sequence. However, in the latter case amino acid changes are preferably of a minor nature, that is conservative amino acid substitutions that do not significantly affect the folding or activity of the polypeptide, small deletions, typically of one to about 30 amino acids; small amino- or carboxyl-terminal extensions, small linker peptide of up to about 20–25 residues, or a small extension that facilitates purification, such as a poly-histidine tract, an antigenic epitope or a binding domain. See in general Ford et al., (1991), Protein Expression and Purification 2, 95–107. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions can be made outside the regions critical to the function of the molecule and still result in an active enzyme. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (Cunningham and Wells, (1989), Science 244, 1081–1085). In the latter technique mutations are introduced at every residue in the molecule, and the resulting mutant molecules are tested for biological (i.e. dextranase) activity to identify amino acid residues that are critical to the activity of the molecule. Sites of substrate-enzyme interaction can also be determined by analysis of crystal structure as determined by such techniques as nuclear magnetic resonance, crystallography or photoaffinity labelling. See, for example, de Vos et al. (1992), Science 255, 306–312; Smith et al., (1992), J. Mol. Biol., 224, 899–904; Wlodaver et al., (1992), FEBS Lett., 309, 59–64.

It will be understood that any partial DNA sequence within the protein coding part of the DNA sequence shown in SEQ ID no. 1 and/or the DNA sequence transformed into the deposited strain *E. coli* DSM 10706 may be used for isolating the entire DNA sequence encoding the recombinant dextranase of the invention. The amino acid sequence (as deduced from the DNA sequence shown in SEQ ID no. 1) is shown in SEQ ID no. 2.

The homology referred to in i) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., (1970), Journal of Molecular Biology, 48, p. 443–453). Using GAP (version 8) with the following settings for DNA sequence comparison: GAP creation penalty of 5.0 and GAP extension penalty of 0.3, the coding region of the DNA sequence exhibits a degree of identity preferably of at least 80%, such as at least 90%, preferably at least 95%, especially at least 99%, with the coding region of the DNA sequence shown in SEQ ID No. 1 or the DNA sequence obtainable from the plasmid in *E. coli* DSM 10706.

The hybridization referred to in ii) above is intended to indicate that the analogous DNA sequence hybridizes to the same probe as the DNA sequence encoding the dextranase under certain specified conditions which are described in detail in the Materials and Methods section hereinafter.

Normally, the analogous DNA sequence is highly homologous to the DNA sequence such as at least 80% homologous to the DNA sequence shown in SEQ ID no. 1 or the DNA sequence obtainable from the plasmid in *E. coli* DSM 10706 encoding a dextranase of the invention, such as at least 90%, preferably at least 95%, such as at least 99% homologous to said DNA sequence shown in SEQ ID no. 1 and/or the DNA sequence obtainable from the plasmid in *E. coli* DSM 10706.

The homology referred to in iii) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., (1970), Journal of Molecular Biology, 48, p. 443–453). Using GAP with the following settings for DNA sequence comparison: GAP creation penalty of 5.0 and GAP extension penalty of 0.3, the coding region of the DNA sequence exhibits a degree of identity preferably of at least 80%, such as at least 90%, preferably at least 95%, especially at least 99%, with the coding region of the DNA sequence shown in SEQ ID no. 1 and/or the DNA sequence obtainable from the plasmid in *E. coli* DSM 10706.

The term "derived from" in connection with property iv) above is intended not only to indicate a dextranase produced by a strain of DSM 10706, but also a dextranase encoded by a DNA sequence isolated from strain DSM 10706 and produced in a host organism transformed with said DNA sequence. The immunological reactivity may be determined by the method described in the "Materials and Methods" section below.

In further aspects the invention relates to an expression vector harbouring a DNA construct of the invention, a cell comprising the DNA construct or expression vector and a method of producing an enzyme exhibiting dextranase activity which method comprises culturing said cell under conditions permitting the production of the enzyme, and recovering the enzyme from the culture.

It is also an object of the invention to provide an enzyme preparation enriched with the recombinant dextranase of the invention.

Further, the invention provides an oral care composition which further comprises an enzyme exhibiting an enzyme activity selected from the group of mutanases, oxidases, peroxidases, haloperoxidases, laccases, proteases, endoglucosidases, lipases, amylases, anti-microbial enzymes, and mixtures thereof.

Finally the invention relates to the use of the recombinant dextranase of the invention. The enzyme of the invention or a composition of the invention comprising such an enzyme may be used for preventing dental caries, plaque or/and tartar.

DETAILED DESCRIPTION OF THE INVENTION

Cloning

The DNA sequence coding for an enzyme exhibiting dextranase activity of the invention may conveniently be isolated from DNA from a suitable source, such as any of the below mentioned organisms, by use of synthetic oligonucleotide probes prepared on the basis of a DNA sequence disclosed herein.

For instance, a suitable oligonucleotide probe may be prepared on the basis of the nucleotide sequences shown in SEQ ID no. 1 and/or the nucleotide sequence obtainable from the plasmid in E. coli DSM 10706, or the amino acid sequence shown in SEQ ID no. 2 or any suitable subsequence thereof.

According to this method primers able to code for these peptides, being a part of SEQ ID No. 2, are designed. Fragments of the gene to be cloned is then PCR amplified by the use of these primers. These fragments are used as probes for cloning the complete gene.

A more detailed description of the screening method is given in Example 1 and 2 below.

Alternatively, the DNA sequence of the invention encoding an enzyme exhibiting dextranase activity may be isolated by a general method involving cloning, in suitable vectors, a DNA library from *Paecilomyces lilacinus*, transforming suitable host cells with said vectors, culturing the host cells under suitable conditions to express any enzyme of interest encoded by a clone in the DNA library, screening for positive clones by determining any dextranase activity of the enzyme produced by such clones, and isolating the DNA coding an enzyme from such clones.

The general method is further disclosed in WO 93/11249 the contents of which are hereby incorporated by reference.

The DNA sequence coding for the recombinant dextranase of the invention may for instance be isolated by screening a cDNA library of the donor organism, and selecting for clones expressing the appropriate enzyme activity (i.e. dextranase activity as defined by the ability of the enzyme to hydrolyse AZCL-Dextran). The appropriate DNA sequence may then be isolated from the clone by standard procedures.

Depositing of the Dextranase Sequence

The complete full length DNA sequence obtained from a strain of *Paecilomyces lilacinus* encoding the dextranase of the invention has been transformed into a strain of the bacteria E. coli DH5α, comprised in the plasmid pUC19. Said bacteria has been deposited by the inventors according to the Budapest Treaty on the International Recognition of the Deposit of Microorganisms for the Purposes of Patent Procedure at the Deutshe Sammlung von Mikroorganismen und Zellkulturen GmbH., Mascheroder Weg 1b, D-38124 Braunschweig Federal Republic of Germany, (DSM).

| Deposit date: | June 7, 1996 |
|---|---|
| Depositor's ref.: | NN49245 = ToC 1065 |
| DSM designation: | E. coli DSM no. 10706 |

Being an International Depository Authority under the Budapest Treaty, Deutshe Sammlung von Mikroorganismen und Zellkulturen GmbH., affords permanence of the deposit in accordance with the rules and regulations of said treaty, vide in particular Rule 9. Access to the deposit will be available during the pendency of this patent application to one determined by the Commisioner of the United States Patent and Trademark Office to be entitled thereto under 37 C.F.R. Par. 1.14 and 35 U.S.C. Par. 122. Also, the above mentioned deposits fulfil the requirements of European patent applications relating to microorganisms according to Rule 28 EPC.

The above mentioned deposit represents a substantially pure culture of the isolated bacteria. The deposit is available as required by foreign patent laws in countries wherein counterparts of the subject application, or its progeny are filed. However, it should be understood that the availability of the deposited strain does not constitute a license to practice the subject invention in derogation of patent rights granted by governmental action.

The DNA sequence encoding the enzyme exhibiting dextranase activity can for instance be isolated from the above mentioned deposited strain by standard methods.

Microbial Sources

It is expected that a DNA sequence coding for a homologous enzyme, i.e. an analogous DNA sequence, is obtainable from other micro-organisms, such as the following filamentous fungi, yeasts or bacteria. For instance, the DNA sequence may be derived from a strain of Paecilomyces, such as *Paecilomyces lilacinus*, or a strain of Penicillium, such as *Penicillium lilacinum* or *Penicillium minioluteum*, Aspergillus, Fusarium, Spicaria, Verticillium, Helminthosporium or Chaetomium; bacteria of the genera Lactobacillus, Streptococcus, Cellvibrio, Cytophaga, Brevibacterium, Pseudomonas, Corynebacterium, Arthrobacter and Flavobacterium; yeasts, such as *Lipomyces starkeyi*.

Production of the Dextranase

The DNA sequence encoding the dextranase may subsequently be inserted into a recombinant expression vector. This may be any vector which may conveniently be subjected to recombinant DNA procedures, and the choice of vector will often depend on the host cell into which it is to be introduced.

Thus, the vector may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the dextranase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the dextranase, the promoter and the terminator, respectively, and to insert them into suitable vectors are well known to persons skilled in the art (cf., for instance, Sambrook et al., (1989), Molecular Cloning. A Laboratory Manual, Cold Spring Harbor, N.Y.).

The host cell which is transformed with the DNA sequence encoding the dextranase is preferably a filamentous fungus cell. In particular, the cell may belong to a species of Aspergillus, most preferably *Aspergillus oryzae* or *Aspergillus niger*, or a strain of Fusarium, such as a strain of *Fusarium oxysporium, Fusarium graminearum* (in the perfect state named *Gribberella zeae*, previously *Sphaeria zeae*, synonym with *Gibberella roseum* and *Gibberella roseum f. sp. cerealis*), or *Fusarium sulphureum* (in the prefect state named *Gibberella puricaris*, synonym with *Fusarium trichothecioides, Fusarium bactridioides, Fusarium sambucium, Fusarium roseum,* and *Fusarium roseum* var. *graminearum*), *Fusarium cerealis* (synonym with *Fusarium crokkwellnse*), or *Fusarium venenatum*.

The host cell may advantageously be a *F. graminearum* described in WO 96/00787 (from Novo Nordisk A/S), e.g. the strain deposited as *Fusarium graminearum* ATCC 20334. The strain ATCC 20334 was previously wrongly classified as *Fusarium graminearum* (Yoder, W. and Christianson, L. 1997). RAPD-based and classical taxonomic analyses have now revealed that the true identity of the Quorn fungus, ATCC 20334, is *Fusarium venenatum* Nirenburg sp. nov.

In the Examples below expression of dextranase is illustrated using *A. oryzae* and *F. venenatum* as host cells.

In a preferred embodiment of the invention the host cell is a protease deficient of protease minus strain.

This may for instance be the protease deficient strain *Aspergillus oryzae* JaL125 having the alkaline protease gene named "alp" deleted. This strain is described in PCT/DK97/00135 (from Novo Nordisk A/S).

Filamentous fungi cells may be transformed by a process involving protoplast formation and transformation of the protoplasts followed by regeneration of the cell wall in a manner known per se. The use of Aspergillus as a host micro-organism is described in EP 238 023 (Novo Nordisk A/S), the contents of which are hereby incorporated by reference.

A Method of Producing an Enzyme of the Invention

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed dextranase may conveniently be secreted into the culture medium and may be recovered there from by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The Enzyme

The invention also relates to an isolated recombinant enzyme with dextranase activity having essentially an amino acid sequence as shown in SEQ ID no. 2 or a fragment of the same. Mass spectrometry showed that the average mass of the recombinant dextranase is about 65.3 kD.

Figure 4:
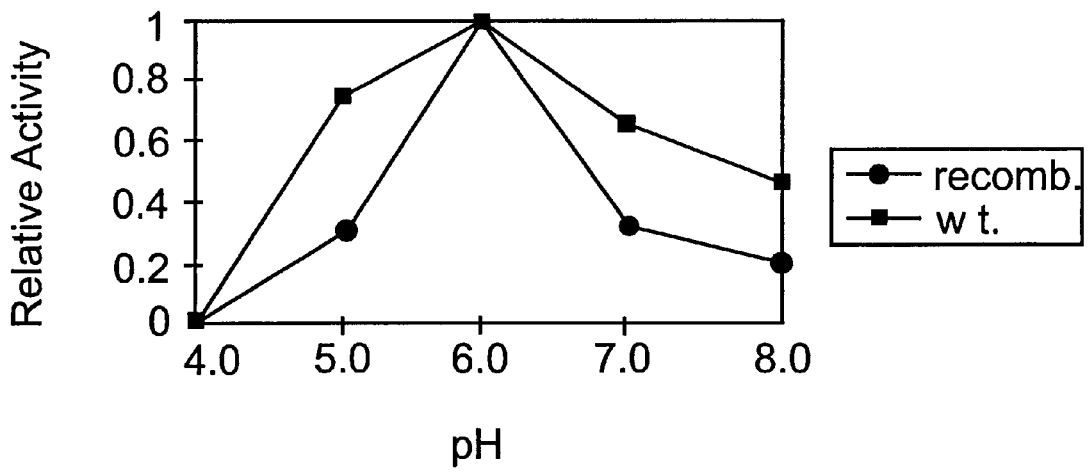
FIG. 4 shows the pH-profile of recombinant and wild-type *Paecilomyces lilacinus* dextranase

The pH optimum of the recombinant dextranase was found to lie in the range from 3.5 to 5.5 which equals the pH optimum of the wild-type dextranase (see FIG. 4). The temperature optimum of both the recombinant and wild-type dextranase was found to be around 60° C. at pH 5.5 (see FIG. 2). Further, the recombinant and wild-type dextranases were stabile at 60° C. at pH 5.5 and pH 7. At 70° C. only little residual activity was observed.

Oral Care Composition

In a still further aspect, the present invention relates to an oral care composition useful as ingredient in oral care products.

An oral care composition of the invention may suitably comprise an amount of the recombinant *Paecilomyces lilacinus* dextranase equivalent to an enzyme activity, calculated as enzyme activity units in the final oral care product, in the range from 0.001 KDU to 1000 KDU/ml, preferably from 0.01 KDU/ml to 500 KDU/ml, especially from 0.1 KDU/ml to 100 KDU/ml.

It is also contemplated according to the invention to include other enzyme activities than dextranase activity in the oral care composition. Contemplated enzyme activities include activities from the group of enzymes comprising mutanases, oxidases, such as glucose oxidase, L-amino acid oxidase, peroxidases, such as e.g. the Coprinus sp. peroxidases described in WO 95/10602 (from Novo Nordisk A/S) or lactoperoxidaseor, haloperoxidases, laccases, proteases, such as papain, acidic protease (e.g. the acidic proteases described in WO 95/02044 (Novo Nordisk A/S)), endoglucosidases, lipases, amylases, including amyloglucosidases, such as AMG (from Novo Nordisk A/S), anti-microbial enzymes, and mixtures thereof.

Oral Care Products

The oral care product may have any suitable physical form (i.e. powder, paste, gel, liquid, ointment, tablet etc.). An "oral care product" can be defined as a product which can be used for maintaining or improving the oral hygiene in the mouth of humans and animals, by preventing dental caries, preventing the formation of dental plaque and tartar, removing dental plaque and tartar, preventing and/or treating dental diseases etc.

At least in the context of the present invention oral care products do also encompass products for cleaning dentures, artificial teeth and the like.

Examples of such oral care products include toothpaste, dental cream, gel or tooth powder, odontic, mouth washes, pre- or post brushing rinse formulations, chewing gum, lozenges, and candy.

Toothpastes and tooth gels typically include abrasive polishing materials, foaming agents, flavouring agents, humectants, binders, thickeners, sweetening agents, whitening/bleaching/stain removing agents, water, and optionally enzymes.

Mouth washes, including plaque removing liquids, typically comprise a water/alcohol solution, flavour, humectant, sweetener, foaming agent, colorant, and optionally enzymes.

Abrasives

Abrasive polishing material might also be incorporated into the dentifrice product of the invention. According to the invention said abrasive polishing material includes alumina and hydrates thereof, such as alpha alumina trihydrate, magnesium trisilicate, magnesium carbonate, kaolin, aluminosilicates, such as calcined aluminum silicate and aluminum silicate, calcium carbonate, zirconium silicate, and also powdered plastics, such as polyvinyl chloride, polyamides, polymethyl methacrylate, polystyrene, phenol-formaldehyde resins, melamine-formaldehyde resins, urea-formaldehyde resins, epoxy resins, powdered polyethylene, silica xerogels, hydrogels and aerogels and the like. Also suitable as abrasive agents are calcium pyrophosphate, water-insoluble alkali metaphosphates, dicalcium phosphate and/or its dihydrate, dicalcium orthophosphate, tricalcium phosphate, particulate hydroxyapatite and the like. It is also possible to employ mixtures of these substances.

Dependent on the oral care product the abrasive product may be present in from 0 to 70% by weight, preferably from 1% to 70%. For toothpastes the abrasive material content typically lies in the range of from 10% to 70% by weight of the final toothpaste product.

Humectants are employed to prevent loss of water from e.g. toothpastes. Suitable humectants for use in oral care products according to the invention include the following compounds and mixtures thereof: glycerol, polyol, sorbitol, polyethylene glycols (PEG), propylene glycol, 1,3-propanediol, 1,4-butanediol, hydrogenated partially hydrolysed polysaccharides and the like. Humectants are in general present in from 0% to 80%, preferably 5 to 70% by weight in toothpaste.

Silica, starch, tragacanth gum, xanthan gum, extracts of Irish moss, alginates, pectin, cellulose derivatives, such as hydroxyethyl cellulose, sodium carboxymethyl cellulose and hydroxypropyl cellulose, polyacrylic acid and its salts, polyvinylpyrrolidone, can be mentioned as examples of suitable thickeners and binders, which helps stabilizing the dentifrice product. Thickeners may be present in toothpaste creams and gels in an amount of from 0.1 to 20% by weight, and binders to the extent of from 0.01 to 10% by weight of the final product.

Foaming Agents

As foaming agent soap, anionic, cationic, non-ionic, amphoteric and/or zwitterionic surfactants can be used. These may be present at levels of from 0% to 15%, preferably from 0.1 to 13%, more preferably from 0.25 to 10% by weight of the final product.

Surfactants

Surfactants are only suitable to the extent that they do not exert an inactivation effect on the present enzymes. Surfactants include fatty alcohol sulphates, salts of sulphonated mono-glycerides or fatty acids having 10 to 20 carbon atoms, fatty acid-albumen condensation products, salts of fatty acids amides and taurines and/or salts of fatty acid esters of isethionic acid.

Sweetening Agents

Suitable sweeteners include saccharin.

Flavouring Agents

Flavours, such as spearmint, are usually present in low amounts, such as from 0.01% to about 5% by weight, especially from 0.1% to 5%.

Whitening/Bleaching Agents

Whitening/bleaching agents include $H_2O_2$ and may be added in amounts less that 5%, preferably from 0.25 to 4%, calculated on the basis of the weight of the final product.

The whitening/bleaching agents may be an enzyme, such as an oxidoreductase. Examples of suitable teeth bleaching enzymes are described in WO 97/06775 (from Novo Nordisk A/S).

Water

Water is usually added in an amount giving e.g. toothpaste a flowable form.

Additional Agents

Further water-soluble anti-bacterial agents, such as chlorhexidine digluconate, hexetidine, alexidine, quaternary ammonium anti-bacterial compounds and water-soluble sources of certain metal ions such as zinc, copper, silver and stannous (e.g. zinc, copper and stannous chloride, and silver nitrate) may also be included.

Also contemplated according to the invention is the addition of compounds which can be used as fluoride source, dyes/colorants, preservatives, vitamins, pH-adjusting agents, anti-caries agents, desensitizing agents etc.

Enzymes

Other essential components used in oral care products and in oral care products of the invention are enzymes. Enzymes are biological catalysts of chemical reactions in living systems. Enzymes combine with the substrates on which they act forming an intermediate enzyme-substrate complex. This complex is then converted to a reaction product and a liberated enzyme which continue its specific enzymatic function.

Enzymes provide several benefits when used for cleansing of the oral cavity. Proteases break down salivary proteins, which are adsorbed onto the tooth surface and form the pellicle, the first layer of resulting plaque. Proteases along with lipases destroy bacteria by lysing proteins and lipids which form the structural components of bacterial cell walls and membranes.

Dextranase breaks down the organic skeletal structure produced by bacteria that forms a matrix for bacterial adhesion. Proteases and amylases, not only prevents plaque formation, but also prevents the development of calculus by breaking-up the carbohydrate-protein complex that binds calcium, preventing mineralization.

A toothpaste produced from an oral care composition of the invention (in weight % of the final toothpaste composition) may typically comprise the following ingredients:

| | |
|---|---|
| Abrasive material | 10 to 70% |
| Humectant | 0 to 80% |
| Thickener | 0.1 to 20% |
| Binder | 0.01 to 10% |
| Sweetener | 0.1% to 5% |
| Foaming agent | 0 to 15% |
| Whitener | 0 to 5% |
| Enzymes | 0.0001% to 20% |

In a specific embodiment of the invention the oral care product is toothpaste having a pH in the range from 6.0 to about 8.0 comprising

| | |
|---|---|
| a) 10% to 70% | Abrasive material |
| b) 0 to 80% | Humectant |
| c) 0.1 to 20% | Thickener |
| d) 0.01 to 10% | Binder |
| e) 0.1% to 5% | Sweetener |
| f) 0 to 15% | Foaming agent |
| g) 0 to 5% | Whitener |
| i) 0.0001% to 20% | Enzymes. |

Said enzymes referred to under i) include the recombinant dextranase of the invention, and optionally other types of enzymes mentioned above known to be used in toothpastes and the like.

A mouth wash produced from an oral care composition of the invention (in weight % of the final mouth wash composition) may typically comprise the following ingredients:

| | |
|---|---|
| 0–20% | Humectant |
| 0–2% | Surfactant |
| 0–5% | Enzymes |
| 0–20% | Ethanol |
| 0–2% | Other ingredients (e.g. flavour, sweetener active ingredients such as florides). |
| 0–70% | Water |

The mouth wash composition may be buffered with an appropriate buffer e.g. sodium citrate or phosphate in the pH-range 6–7.5.

The mouth wash may be in none-diluted form (i.e. must be diluted before use).

Method of Manufacture

The oral care composition and products of the present invention can be made using methods which are common in the oral product area.

Use

According to the present invention the recombinant dextranase or compositions comprising a such are useful for a number of applications including the use in oral care products for humans and/or animals for preventing the formation of dental plaque or removing dental plaque; the use for hydrolysis of sugar juice or syrup; the use in food, feed and/or pet food products.

MATERIALS AND METHODS

Materials

Micro-organisms

*E. coli* DSM no. 10706 deposited according to the Budapest Treaty on the International Recognition of the Deposit of Micro-organisms for the Purposes of Patent Procedure at the Deutshe Sammlung von Mikroorganismen und Zellkulturen GmbH., Mascheroder Weg 1b, D-38124 Braunschweig Federal Republic of Germany, (DSM).

*A. oryzae* JaL 125: *Aspergillus oryzae* IFO 4177 available from Institute for Fermention, Osaka; 17–25 Juso Hammachi 2-Chome Yodogawa-ku, Osaka, Japan, having the alkaline protease gene named "alp" (described by Murakami K et al., (1991), Agric. Biol. Chem. 55, p. 2807–2811) deleted by a one step gene replacement method (described by G. May in "Applied Molecular Genetics of Filamentous Fungi" (1992), p. 1–25. Eds. J. R. Kinghorn and G. Turner; Blackie Academic and Professional), using the *A. oryzae* pyrG gene as marker.

Fusarium CC1-3: A morphological mutant of Fusarium A3/5 (ATCC 20334) (Wiebe et al., 1992, Mycological Research 96: 555–562; Wiebe et al., 1991, Mycological Research 95: 1284–1288; Wiebe et al., 1991, Mycological Research 96: 555–562) is a highly branched, colonial variant. Strain ATTC 20334 is the strain referred to in WO 96/00787 as *Fusarium graminearum* ATTC 20334. Strain ATTC 20334 was previously wrongly classified as *F. graminearum* (Yoder and Christianson, (1997). RAPD-based and classical taxonomic analyses reveal the true identity of the Quorn fungus, ATCC 20334, to be *Fusarium venenatum* Nirenburg sp. nov.

*E. coli* DH5α

*E. coli* strain JM101

Figure 2:
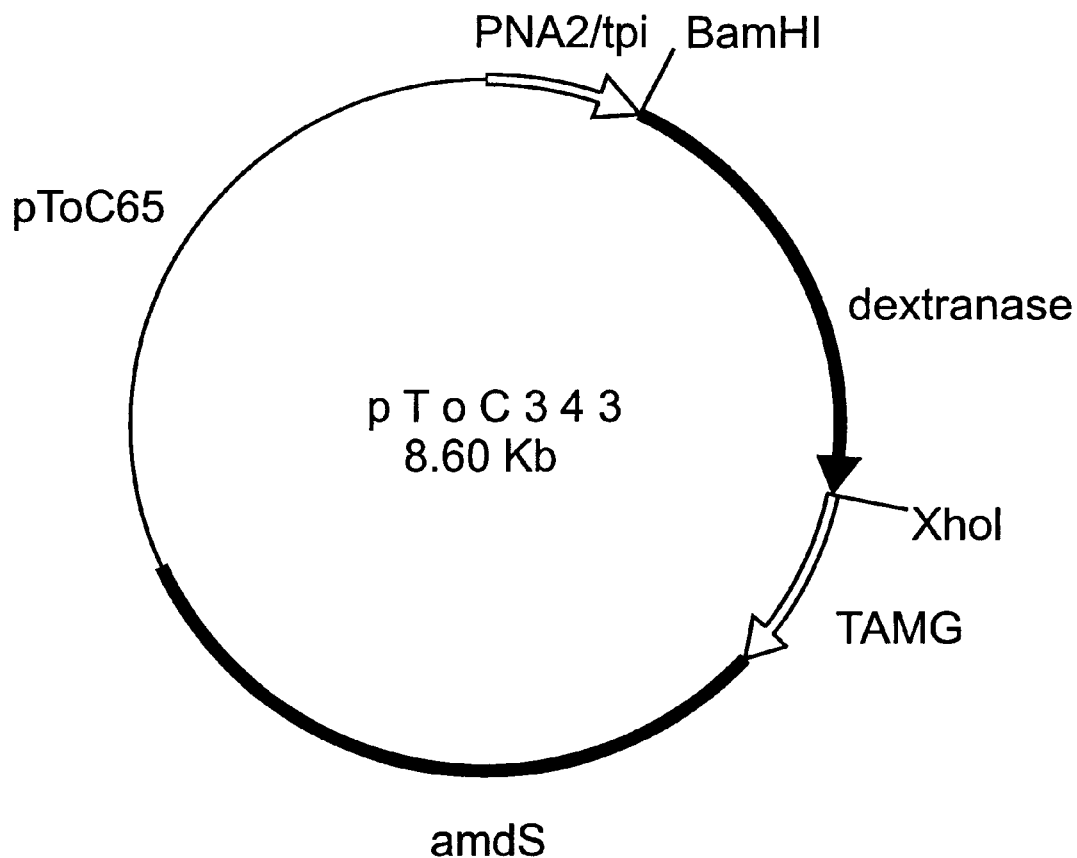
FIG. 2 shows plasmid pToC343
Figure 3:
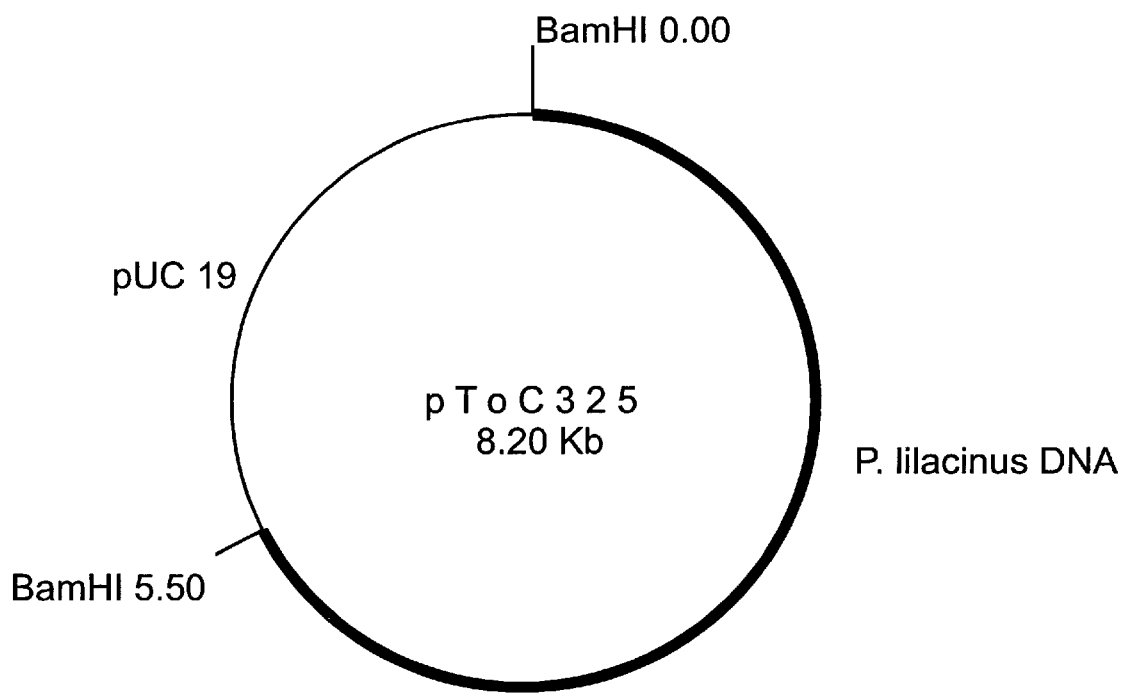
FIG. 3 shows plasmid pToC325

Plasmids and Vectors pCaHj483 (FIG. 1)

pToC343 (FIG. 2)

pToC325 (FIG. 3)

pICAMG/Term (EP 238 023)

pUC19 (Yanish-Perron et al., (1985), Gene 33, p. 103–119)

pJW111: Expression plasmid (FIG. 8) built and amplified in *Escherichia coli* strain JM101.

pDM181: The Fusarium expression plasmid (Jones et al. (1996)) is a single vector system that encodes the SP387 promoter and terminator, as well as the bar gene (Thompson et al., (1987), EMBO, 6 (9): 2519–2514) which confers Basta resistance. Two restriction enzyme sites, those for SwaI and PacI, have been introduced between the SP387 regulatory sequences to facilitate cloning.

Enzymes

Dextranase L50 produced by *Paecilomyces lilacinus* (Novo Nordisk A/S).

lysyl-specific protease from Achromobacter

NOVOZYM 234™ (Novo Nordisk A/S)

Media, Substrates and Solutions

YPG medium: 1% yeast extract, 2% bactopeptone, and 2% glucose

YPD: 10 g yeast extract, 20 g peptone, $H_2O$ to 900 ml. Autoclaved, 100 ml 20% glucose (sterile filtered) added.

Dextran 500 (Pharmacia)

AZCL-dextran (MegaZyme).

pCRII (Invitrogen TA Cloning Kit)

Britton-Robinson Buffer

DAPI: 4',6-diamidino-2-phenylindole (Sigma D-9542)

BHI: Brain Heart Infusion broth

Vogel's/Basta medium: Vogel's salts (Vogel, H. J. (1964), Am. Nat. 98:436–446), 25 mM $NaNO_3$, 5 mg/ml Basta (Hoechst), 25 g/L sucrose, 25 g/L noble agar, pH 6.0.

M400Da medium: 50 g of maltodextrin, 2.0 g of $MgSO_4$-$7H_2O$, 2.0 g of $KH_2PO_4$, 4.0 g of citric acid, 8.0 g of yeast extract, 2.0 g of urea, and 0.5 ml of trace metals solution per liter. The medium is adjusted to pH 6.0 with 5 N NaOH. The trace metals solution is comprised of 14.3 g of $ZnSO_4$-$7H_2O$, 2.5 g of $CuSO_4$-$5H_2O$, 0.5 g of $NiCl_2$-$6H_2O$, 13.8 g of $FeSO_4$-$7H_2O$, 8.5 g of $MnSO_4$-$H2O$, and 3.0 g of citric acid per liter.

Sporulation medium: 12.1 g/L $NaNO_3$, 25 g/L succinic acid(disodium salt), 1 g/L glucose and 1×Vogel's salts adjusted to pH 6.0.

STC: 0.8 M sorbitol, 25 mM Tris pH 8.0, 50 mM $CaCl_2$

SPTC: 40% PEG4000, 0.8M sorbitol, 25 mM Tris pH 8.0, 50 mM $CaCl_2$.

Equipment 10 kDa cut-off ultra-filtration cassette (Alpha Minisette from Filtron).

Phenyl-sepharose FF (high sub) column (Pharmacia)

Seitz EK1 filter plate

Q-sepharose FF column (Pharmacia)

Applied Biosystems 473A protein sequencer 2 liter Kieler fermenter

Olympus model BX50 microscope

Malthus Flexi M2060 (Malthus Instrument Limited)

Primers

8001 GA(A/G)AA(T/C)TA(T/C)GC(T/C/G/A)TA(T/C)ATGGC (SEQ ID No 15)

8002 GCCAT(G/A)TA(G/A/T/C)GC(A/G)TA(G/A)TT(T/C)TC (SEQ ID No 16)

8003 TGGAC(A/G/T/C)CA(A/G)TT(T/C)CA(A/G)TA(T/C)GC (SEQ ID No 17)

8004 GC(A/G)TA(T/C)TG(A/G)AA(T/C)TG(A/G/T/C)GTCC (SEQ ID No 18)

8005 AA(T/C)TGGCA(A/G)AT(T/C/A)GG(A/G/T/C)GG (SEQ ID No 19)

8006 CC(A/G/T/Q)CC(T/A/G)TA(T/C)TGCCA(A/G)TT (SEQ ID No 20)

8864 CGCGGATCCACCATGCGTTGGCCTGG-
TAATTTTC (SEQ ID No 23)

8867 CCGCTCGAGCCTGCCTCATTCAATGCTCC (SEQ ID No 24)

Methods

Dextranase Activity Assay

The Dextranase activity assay measures the release of reducing sugars from dextran with alkalic 3,5-dinitrosalicylic acid (adsorption at 540 nm).

Conditions: 2.5% Dextran 500 (Pharmacia) in 0.1 M sodium acetate, pH 5.4 at 40° C. Enzyme concentrations around 1 DU/ml.

1 DU equals the amount of enzyme that produces an amount of reducing sugars equivalent to 1 mg of maltose in 1 hour.

Dextranase activity can also be measured using AZCL-dextran (MegaZyme). 500 µl 0.4% AZCL-dextran in 0.1 M sodium acetate, pH 5.5 or 50 mM Britton-Robinson buffer is added 500 µl enzyme sample diluted in MilliQ filtered $H_2O$ and incubated for 10 minutes at 40° C. Then the samples are centrifuged for 2 minutes at 15,000 g and 200 µl of supernatant is added to wells in a microtiter plate and the absorption at 595 nm is measured.

Molecular Characterization of Wild-type Dextranase from *Paecilomyces lilacinus*

Mass Spectrometry

Mass spectrometry of purified wild type dextranase is done using matrix assisted laser desorption ionisation time-of-flight mass spectrometry in a VG Analytical TofSpec. For mass spectrometry 2 ml of sample is mixed with 2 ml saturated matrix solution (α-cyano-4-hydroxycinnamic acid in 0.1% TFA:acetonitrile (70:30)) and 2 ml of the mixture spotted onto the target plate. Before introduction into the mass spectrometer the solvent is removed by evaporation. Samples are desorbed and ionised by 4 ns laser pulses (337 nm) at threshold laser power and accelerated into the field-free flight tube by an accelerating voltage of 25 kV. Ions are detected by a microchannel plate set at 1850 V.

Preparation of Hydroxyapatite Disks (HA)

Hydroxyapatite tablets are prepared by compressing 250 mg of hydroxyapatite in a tablet die at about 5,900 kg (13,000 lbs) of pressure for 5 minutes. The tablets are then sintered at 600° C. for 4 hours and finally hydrated with sterile deionized water.

Plaque Coating of Hydroxyapatite Disks (HA)

Hydroxyapatite disks (HA) were dry sterilised (121° C., 2 bar, 20 minutes) and coated with filter sterilised saliva for 18 hours at 37° C. The HA disks were placed in a sterile rack in a beaker, Brain Heart Infusion broth (BHI) containing 0.2% sucrose was poured into the beaker covering the disks. Sterile $Na_2S$ (pH 7.0) was added immediately before inoculation given the final concentration of 5 g/liter. A mixture 1:1:1 of *Streptococcus mutans, Actinomyces viscosus* and *Fusobacterium nucleatum* grown anaerobically (BHI, 37° C., 24 hour) was used as inoculum in the concentration of approximately $10^6$ cfu/ml. The disks were incubated anaerobic at 37° C. for 4 days with slight stirring.

Malthus-method for Plaque

The Malthus-method is based on the methods described in Johnston et al., (1995), Journal of Microbiological Methods 21, p. 15–26 and Johansem et al. (1995), Journal of Applied Bacteriology 78, p. 297–303.

Polymerase Chain Reaction (PCR)

PCR reactions contained components from the Advantage cDNA PCR core kit (Clontech, Palo Alto), 0.1 mg of pToC343 and 50 pmol each of the primers o-dexSwaI {GCATTTAAATATG CGT TGG CCT GGT} and o-dexPacI {CGTTAAT TAA TCA TTC AAT GCT CCA GTC} with the following cycles: 1 cycle of 95° C. for 4 min.; 25 cycles of (95° C. for 1 min, 60° C. for 1 min, 72° C. for 2 min); 1 cycle of 72° C. for 5 min.

EXAMPLES

Example 1

Purification of Wild-type Dextranase

Step 1: Ultra-filtration 1 liter Dextranase 50 L (Novo Nordisk A/S) was mixed with 8 liter 50 mM Na-acetate/HCl, pH 5.4. The mixture was concentrated to approximately 0.5 liter on a 10 kDa cut-off ultra-filtration cassette (Alpha Minisette from Filtron). Another 8 liter 50 mM Na-acetate/HCl, pH 5.4 was added and the enzyme was again concentrated to approx. 0.5 liter.

Step 2: Chromatography on Phenyl-sepharose FF

Saturated ammonium sulphate was added to give a final ammonium sulphate concentration of 1.0M. The pH was adjusted to pH 6.0 with 3% NaOH and the enzyme was filtered on a Seitz EK1 filter plate. The EK1-filtrate was divided in two halves.

A 1 liter Phenyl-sepharose FF (high sub) column was equilibrated in 25mM Na-acetate/HCl, 1.0M $(NH_4)_2SO_4$, pH 6.0. One half of the EK1-filtrate was applied to the column and the column was washed with 5 column volumes of equilibration buffer to remove non-binding proteins. To elute the dextranase an ammonium sulphate gradient (1.0M→0.0M) over 5 column volumes was applied to the column. The Phenyl-sepharose FF column step was repeated with the other half of the EK1-filtrate. Fractions with dextranase activity were pooled.

Step 3: Chromatography on Q-sepharose FF

The pooled fractions were concentrated on a 10 kDa cut-off ultrafiltration cassette to approx. 250 ml. The ultra-filtrated enzyme was dialyzed against 10 mM Na-acetate/HCl, pH 6.0 with several buffer changes.

A 1 liter Q-sepharose FF column was equilibrated in 20 mM Na-acetate/HCl, pH 6.0. The enzyme was applied to the column and the column was washed with equilibration buffer until the $OD_{280}$ signal had returned to baseline. The dextranase enzyme was eluted with a linear NaCl gradient (0→75 mM) over five column volumes.

Fractions from the column were analyzed for dextranase activity and fractions with dextranase activity were analyzed by SDS-PAGE. Fractions which were judged to be at least 90% pure were pooled as the purified Dextranase. Finally the enzyme was filtered through a 0.20 p filter.

Example 2

N-terminal Sequencing of Wild-type Dextranase

N-terminal Amino Acid Sequencing

N-terminal amino acid sequencing was carried out in an Applied Biosystems 473A protein sequencer.

To generate peptides reduced and S-carboxymethylated dextranase, wild-type dextranase (>>500 mg), purified as described in the Materia and Methods section, was digested with the lysyl-specific protease from Achromobacter (20 mg) in 40 mM NH$_4$HCO$_3$ containing 1.3 M urea for 16 hours at 37° C. The resulting peptides were separated by reversed phase HPLC using a Vydac C$_{18}$ column eluted with a linear gradient of 80% 2-propanol containing 0.08% TFA in 0.1% aqueous TFA.

Peptides were re-purified by reversed phase HPLC using a Vydac C$_{18}$ column eluted with linear gradients of 80% acetonitrile containing 0.08% TFA in 0.1% aqueous TFA before subjected to N-terminal amino acid sequencing.

The amino acid sequences determined are given below. Xaa designates unidentified residues and Asx are residues where it has not been possible to distinguish Asp from Asn.

N-terminal
Asp-Gln-Gln-Asn-Gln-Ala-Leu-His-Thr-Trp-Trp-His-Glu-Lys-Ser- (SEQ ID No. 3)

Actually the direct N-terminal amino acid sequencing of the dextranase revealed three sequences staggered with respect to each other. The sequences was found in the ratio 2:1:2 starting at Asp1, Gln3 and Asn4, respectively.

Peptide 1
Ser-Tyr-Val-Asn-Asp-Gly-Gly-Val-Leu-Val-Ser-Glu-Glu-Pro-Arg-Asn-Ala-Leu-Leu-Ile-Phe-Ala-Ser-Pro-Phe-Ile-Pro-Gln (SEQ ID No. 4).

Peptide 2
Ser-Asp-Arg-Thr-Ser-Leu-Arg-Ile-Phe-Ser-His-Gln-Ala-Val-Ser-Asp-Ser-Gln-Ile-Trp-His-Xaa-Ile (SEQ ID NO. 5)

Peptide 3
Asn-Asp-Phe-Tyr-Thr-Val-Gly-His-Gly-Val-Val-Ser-Gly-Glu-Asn-Tyr-Ala-Tyr-Met-Ala-Asn-Thr-Ala-Lys (SEQ ID No. 6)

Peptide 4
Ile-Asn-Ala-Ala-Trp-Thr-Gln-Phe-Gln-Tyr-Ala-Lys (SEQ ID No. 7)

Peptide 5
Asp-Gly-Ser-Ala-Leu-Gly-Pro-Thr-Ser-Asn-Val-Val-Ile-Arg-Pro-Ser-Asp-Ile-Arg-Tyr-Asp-Ile-Ser-Ser-Pro-Asp (SEQ ID No. 8)

Peptide 6
Asn-Trp-Gln-Ile-Gly-Gly-Asn-Arg-Val-Asp-Gly-Ser-Asn-Trp-Gln-Val-Asn-Gln (SEQ ID No. 9)

Peptide 7
Ser-Glu-Thr-Val-Val-Pro-Ser-Ala-Ile-Ile-Gly-Ala-Ser-Pro-Tyr-Tyr-Gly-Asp-Pro (SEQ ID No. 10)

Peptide 8
Leu-Asx-Ala-Asx-Thr-His-Tyr-Val-Tyr-Phe-Glu-Pro-Gly-Thr-Tyr-Ile-Lys (SEQ ID No. 11).

Peptide 9
Val-Ile-His-Thr-Arg-Trp-Phe (SEQ ID No. 12)

Peptide 10
Ser-Ala-Val-Asn-Asp-Ala-Gly-Ala-Val-Ala-Ala-Asp-Glu-Val-Arg-Gln-Ser-Asg-Lys (SEQ ID No. 13)

Peptide 11
Xaa-His-Asn-Asp-Pro-Val-Ile-Gln-Met-Gly-Xaa-Lys (SEQ ID No. 14).

Example 3

Cloning of the Dextranase Gene from *Paecilomyces lilacinus*

The cloning of the dextranase gene from *Paecilomyces lilacinus* was based on the knowledge of the partial amino acid sequence described in Example 2. Degenerate PCR primers able to code for peptide 3, 4 and 6 were designed. Primers coding for the same sequences in both orientations were made. All combinations of the six primers were used in PCR reactions with chromosomal DNA from *Paecilomyces lilacinus*. Some of these reactions resulted in DNA fragments which coded for parts of the dextranase genes. These fragment were used as probes on a genomic Southern. A 6 kb BamHI fragment hybridized and was subsequently cloned and sequenced. All in vitro DNA work was done following standard procedures (Sambrook et al., Molecular Cloning; A Laboratory Manual, 2nd Edition, Cold Spring Harbor Laboratory Press (1989))

PCR Fragments

The following primers were synthesized.
8001 GA(A/G)AA(T/C)TA(T/C)GC(T/C/G/A)TA(T/C)ATGGC
8002 GCCAT(G/A)TA(G/A/T/C)GC(A/G)TA(G/A)TT(T/C)TC
8003 TGGAC(A/G/T/C)CA(A/G)TT(T/C)CA(A/G)TA(T/C)GC
8004 GC(A/G)TA(T/C)TG(A/G)AA(T/C)TG(A/G/T/C)GTCC
8005 AA(T/C)TGGCA(A/G)AT(T/C/A)GG(A/G/T/C)GG
8006 CC(A/G/T/C)CC(T/A/G)TA(T/C)TGCCA(A/G)TT The primers 8001 and 8002 encode amino acids no. 14–20 of peptide no. 3 in one or the other direction. Primers 8003 and 8004 encode amino acids no. 5–11 of peptide no. 4 and primers 8005 and 8006 encode amino acids no. 1–6 of peptide no. 6. Chromosomal DNA from *Paecilomyces lilacinus* Li-3 was prepared essential as described by Yelton et al. (Proc. Natl. Acad. Sci., (1984), 81, p. 1470–1474).

PCR reactions were run according to standard procedures with all combinations of primers. The primer sets 8001/8006 and 8003/8002 gave fragments that upon cloning in the vector pCRII (Invitrogen TA Cloning Kit) and sequencing on an Applied Biosystems DNA Sequencer were shown to contain parts of the dextranase gene. The fragment obtained with the primer-set 8001/8006 was approximately 0.9 kb. Sequencing of the ends of this fragment revealed a DNA sequence encoding peptide no. 2.

The fragment obtained with 8003/8002 were approximately 0.6 kb. Sequencing revealed that sequences encoding peptide 5, 1 and 8 were contained in this fragment.

Genomic Clone

A Southern blot of chromosomal DNA from *Paecilomyces lilacinus* cut with BamHI, BglII, EcoRI, HindIII, SalI, XbaI and XhoI was made and hybridized with the $^{32}$P labelled PCR fragments. Both fragments hybridized to an approximately 6 kb BamHI fragment. A library of approximately 6 kb BamHI fragments from *Paecilomyces lilacinus* cloned into pUC19 was made. The library was screened by colony hybridization with one of the PCR fragments and a positive plasmid pToC325 (See FIG. 2) was isolated. 2994 bp of pToC325 were sequenced, the DNA sequence and the deduced amino acid sequence is shown in SEQ ID No. 1 and SEQ ID No. 2, respectively. pToC325 transformed into *E. coli* DH5α was deposited at DSM as strain no. 10706

Example 4

Expression of Recombinant Dextranase in *Aspergillus oryzae*

Restriction enzyme sites were introduced at the start and stop codon of the dextranase by which the gene was cloned into an *A. oryzae* expression vector, pCaHj483. The resulting dextranase expression plasmid was transformed into an *A. oryzae* strain. Transformants were isolated and analyzed for the expression of dextranase.

Construction of pCaHj483 pCaHj483 (see FIG. 1) was build from the following fragments:

a) The vector pToC65 (WO91/17243) cut with EcoRI and XbaI.
b) A 2.7 kb XbaI fragment from *A. nidulans* carrying the amdS gene (C. M. Corrick et al. (1987), Gene 53, 63–71). The amdS gene is used as a selective marker in fungal transformations. The amdS gene has been modified so that the BamHI site normally present in the gene is destroyed. This has been done by introducing a silent point mutation using the primer: 5'-AGAAATCGGGTATCCTTTCAG-3' (see SEQ ID No. 21)
c) A 0.6 kb EcoRI/BamHI fragment carrying the *A. niger* NA2 promoter fused to a 60 bp DNA fragment of the sequence encoding the 5' un-translated end of the mRNA of the *A. nidulans* tpi gene. The NA2 promoter was isolated from the plasmid pNA2 (EP-B-0 383 779 from Novo Nordisk A/S) and fused to the 60 bp tpi sequence by PCR. The primer encoding the 60 bp tpi sequence had the following sequence:
5'-GCTCCTCATGGTGGATCCCCAGTTGTGTATATAG-AGGATTGAGGAAGGAAGAGAAGTGT GGATAGAGGTAAATTGAGTTGGAAACTCCAAGC-ATGGCATCCTTGC-3' (See SEQ ID No. 22)
d) A 675 bp XbaI fragment carrying the *A. niger* glucoamylase transcription terminator. The fragment was isolated from the plasmid pICAMG/Term (EP 238 023 from Novo Nordisk A/S).

The BamHI site of fragment c was connected to the XbaI site in front of the transcription terminator on fragment d via the pIC19R linker (BamHI to XbaI)

Cloning of Dextranase into pCaHj483

BamHI and a XhoI sites were introduced in front of the ATG and rigth after the stop codon of the dextranase gene by PCR with the following primers:
8864 CGCGGATCCACCATGCGTTGGCCTGG-TAATTTTC (SEQ ID No. 23)
8867 CCGCTCGAGCCTGCCTCATTCAATGCTCC (SEQ ID No. 24)

The gene was re-sequenced to check for PCR errors and cloned via the BamHI and XhoI sites into the expression vector pCaHj483. The resulting dextranase expression plasmid was named pToC343 and is depicted in FIG. 3.

*A. oryzae* Transformants of pToC343

*A. oryzae* JaL 125 was transformed with pToC343 as described in EP 0 238 023. Transformants were selected by their ability to use acetamide as the only nitrogen source. After two re-isolations through conidiospores on minimal acetamid plates the transformants were fermented for four days at 30° C. in 10 ml YPD. Samples of the fermentation broth were applied to SDS-PAGE. The gels were stained by croomasie brillant blue. A band of approximately 65 kD was visible in the broth from the transformants and not in the broth from JaL125.

Three transformants producing the 65 kD protein were fermented in a 2 liter Kieler fermenter for five days in a maltodextrin containing medium and the content of dextranase was determined enzymatically.

The transformant produced up to 11.000 DU/ml in the fermentation broth, the un-transformed host produced less than 100 DU/ml.

Example 5

Purification of Recombinant Dextranase

Culture broth was filtered and concentrated in an Amicon cell (membrane cut off: 10 kDa). The sample was diluted with MilliQ filtered $H_2O$ and pH was adjusted to pH 7.5. The sample was then loaded on to a Q-Sepharose column (Pharmacia) equilibrated in 20 mM sodium phosphate, pH 7.5 and the dextranase was eluted in a linear gradient of 0 to 0.5 M NaCl in 20 mM sodium phosphate, pH 7.5. Dextranase-containing fractions were pooled, added $(NH_4)_2SO_4$ to a concentration of 1 M and loaded onto a Phenyl-Sepharose column (Pharmacia) equilibrated in 1 M $(NH_4)_2SO_4$. The dextranase was eluted in a linear gradient of 1 to 0 M $(NH_4)_2SO_4$.

The N-terminal amino acid sequence of the purified recombinant dextranase was confirmed by N-terminal protein sequencing. Actually two N-terminal amino acid sequences were found; one beginning at Asp1 (Asp-Gln-Gln-Asn-Gln-) and one beginning at Asn4 (Asn-Gln-) in a ratio of 2:3.

Example 6

Molecular Weight of Dextranase

The purified recombinant dextranase like the wild-type enzyme had a molecular weight of around 65 kDa from SDS-PAGE. This was confirmed by matrix assisted laser desorption ionization time-of-flight mass spectrometry, where a molecular weight around 65 kDa was observed.

Mass spectrometry of the wild-type dextranase revealed an average mass around 65.3 kDa.

Example 7 pH-profile of Recombinant and Wild-type Dextranase

Enzyme samples were incubated with AZCL-dextran in 50 mM Britton-Robinson buffer at various pH. Both recombinant and the wild-type dextranase have a pH optimum around pH 6 (see FIG. 4).

Example 8

Temperature Profile of Recombinant and Wild-type Dextranase

Figure 5:
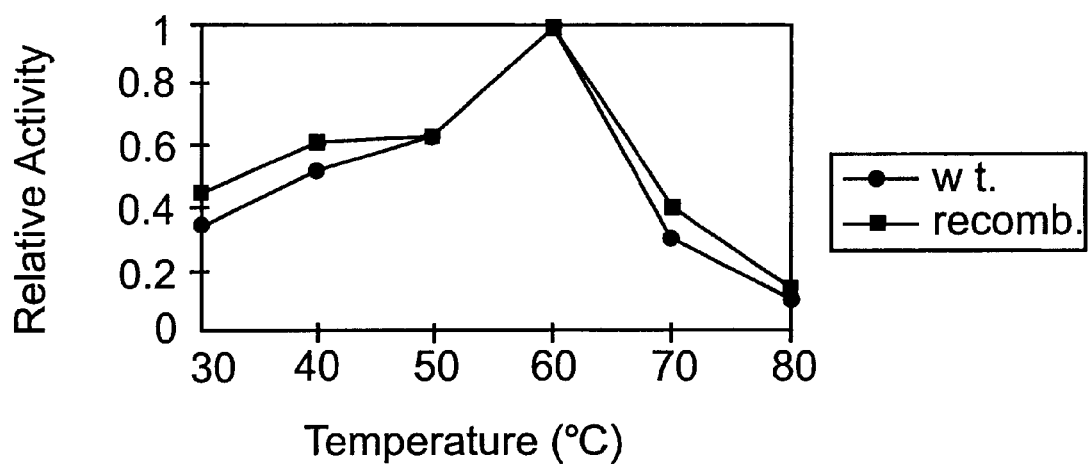
FIG. 5 shows the temperature profile of recombinant and wild-type *Paecilomyces lilacinus* dextranase

Enzyme samples were incubated with AZCL-dextran in 0.1 M sodium acetate, pH 5.5 at various temperatures. The recombinant and the wild-type enzyme has similar temperature profiles with an optimum around 60° C. (see FIG. 5).

Example 9

Temperature Stability of Recombinant and Wild-type Dextranase

Figure 6:
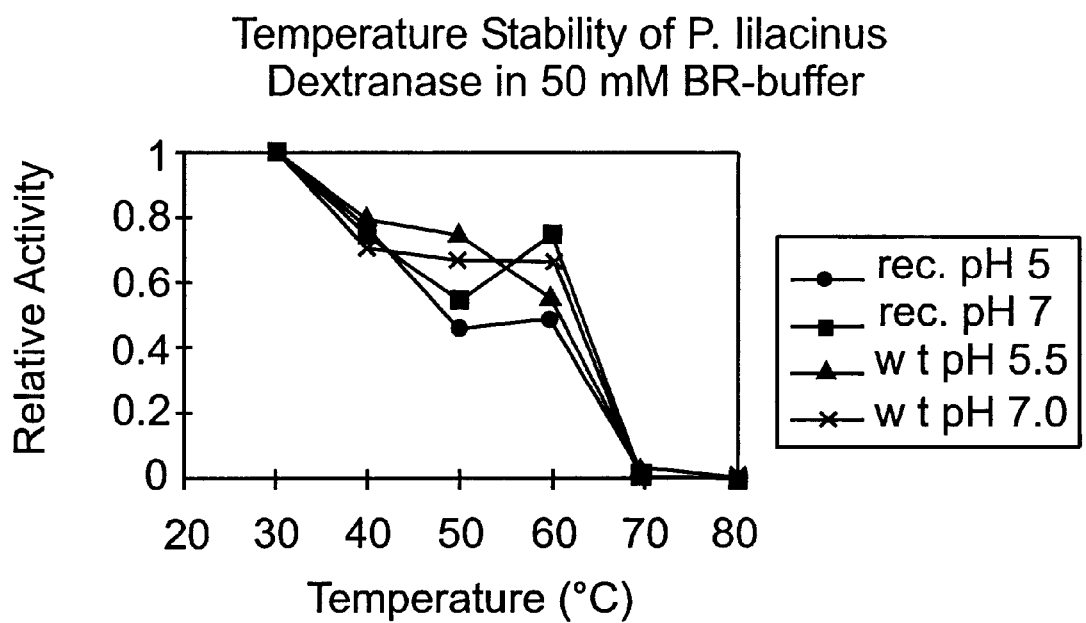
FIG. 6 shows the temperature stability of recombinant and wild-type *Paecilomyces lilacinus* dextranase

Enzyme samples were pre-incubated at various temperatures in 50 mM Britton-Robinson buffer at pH 5.5 or pH 7 for 30 minutes. Then the samples were diluted 10 fold in 0.1 M sodium acetate, pH 5.5 before measuring the residual activity. A comparable temperature stability was obtained for the two enzymes at both pH 5.5 and pH 7. The dextranase is stable at 60° C. After incubation at 70° C. little residual activity is observed (see FIG. 6).

Example 10

Recombinant Dextranase against Dental Plaque

A plaque biofilm was grown anaerobic on saliva coated hydroxyapatite disks as described in the Materials and Methods section above. The plaque was a mixed culture of Streptococcus mutans (SFAG, CBS 350.71), Actinomyces viscosus (DSM no. 43329) and Fusobacterium nucleatum subsp. polymorphum (DSM no. 20482).

HA disks with plaque were transferred to acetate buffer (pH 5.5) containing 1 KDU/ml recombinant Paecilomyces lilacinus dextranase and whirled for 2 minutes (sterile buffer was used as control).

After enzyme treatment, the HA disks were either DAPI stained or transferred to Malthus cells.

Indirect impedance measurements were used when enumerating living adherent cells (Malthus Flexi M2060, Malthus Instrument Limited).

Figure 7:
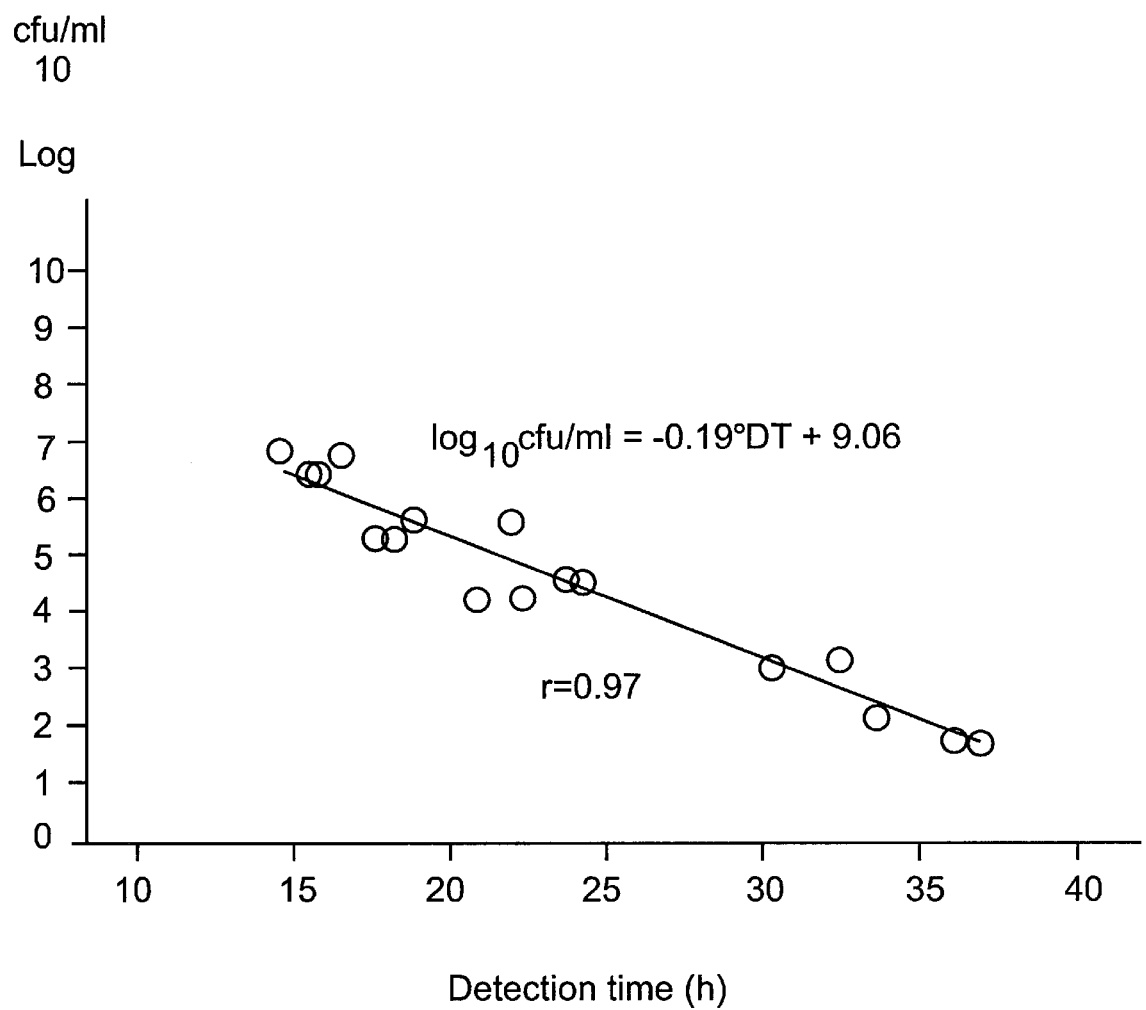
FIG. 7 shows the indirect Malthus standard curve for a mix culture of *S. mutans, A. viscosus* and *F. nucleatum* grown in BHI at 37° C.

For the impedance measurements 3 ml of BHI were transferred to the outer chamber of the indirect Malthus cells, and 0.5 ml of sterile KOH (0.1 M) was transferred to the inner chamber. The HA disks with plaque were after dextranase treatment slightly rinsed with phosphate buffer and transferred to the outer chamber. The detection times (dt) in Malthus were converted to colony counts by use of a calibration curve relating cfu/ml to dt (See FIG. 7).

The calibration curve was constructed by a series 10-fold dilution rate prepared from the mixed culture. Conductance dt of each dilution step was determined in BHI and a calibration curve relating cfu/ml of the 10 fold dilutions to dt in BHI was constructed for the mixed culture.

The removal of plaque from the HA disks was also determined by fluorescent microscopy, disks were after enzyme treatment stained with DAPI (3 mM) and incubated in the dark for 5 minutes at 20° C. The DAPI stained cells were examined with the x 100 oil immersion fluorescence objective on an Olympus model BX50 microscope equipped with a 200 W mercury lamp and an UV-filter. The result was compared with the quantitative data obtained by the impedance measurements.

The number of living cells on the saliva treated HA-surface was after the dextranase treatment determined by the Malthus method and shown in Table 1.

However, by the Malthus method it is not possible to distinguish between a bactericidal activity of the enzyme or an enzymatic removal of the plaque. Therefore a decrease in living bacteria on the surface has to be compared with the simultaneously removal of plaque from the surface which is estimated by the DAPI staining.

TABLE 1

Enzymatic plaque removal (pH 5.5, 2 minutes) from saliva treated hydroxyapatite determined by impedance measurements.

| Dextranase (KDU/ml) | $Log_{10}$ reduction $(cfu/cm^2)$ | Removal of plaque (%) | No. of observations |
|---|---|---|---|
| 0 | 0 | 0 | 10 |
| 1 | 2.5 | 99 | 3 |

A significant removal of plaque was determined by fluorescent microscopy after treatment with dextranase. Thus the recombinant dextranase reduced the amount of adhering cells.

Consequently, the activity was observed as a removal of plaque and not as a bactericidal activity against cells in plaque.

Example 11

Figure 8:
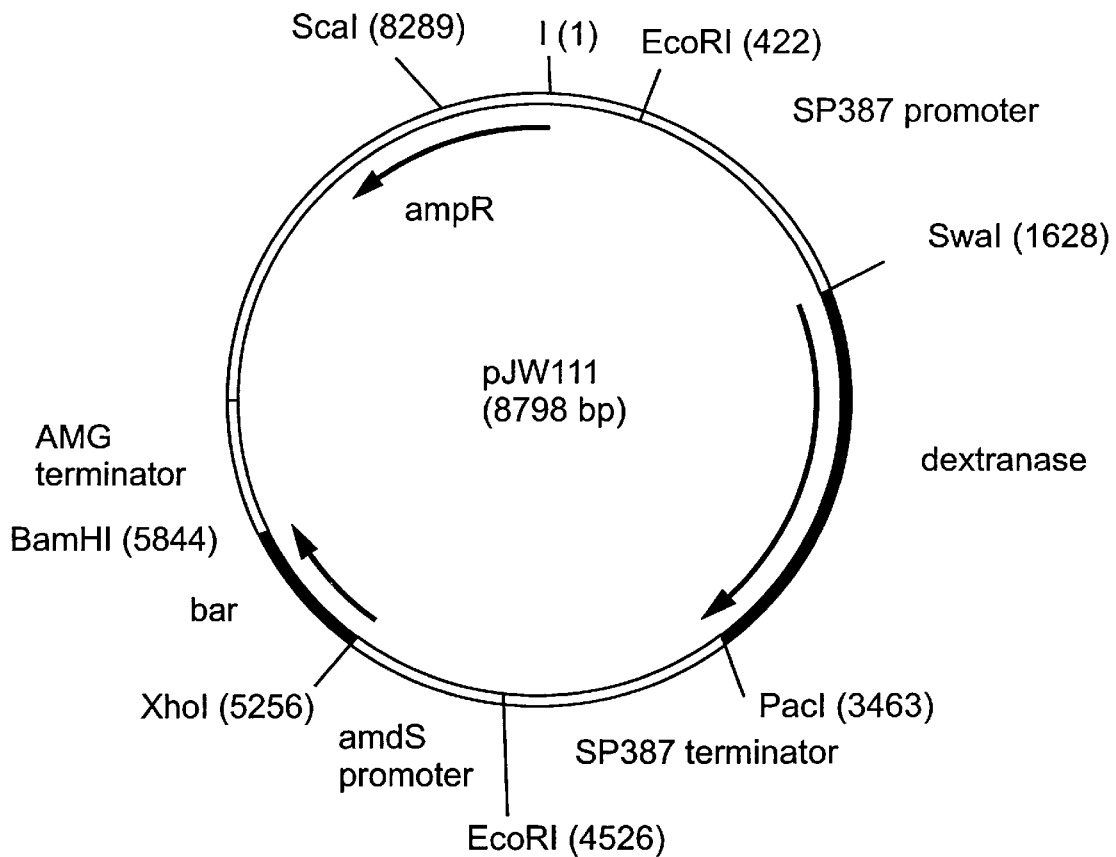
FIG. 8 shows the expression plasmid pJW111. The SP387 promoter and terminator are labelled. Restriction enzyme sites are indicated as well as their relative position within the plasmid. The bar, beta-lactamase (ampR) and dextranase genes are represented by arrows showing the direction of transcription.

Expression of Recombinant Paecilomyces lilacinus Dextranase in Fusarium venenatum Construction of Dextranase Expression Plasmid for F. venenatum The dextranase gene was PCR amplified from the expression plasmid pToC343 using primers o-dexSwa (SEQ ID NO 25) and o-dexPac (SEQ ID NO 26) (see Materials and Methods). The resulting 1860 nt amplicon was digested with SwaI and PacI and ligated to pDM181 that had been linearized with the same two enzymes. The construct was introduced into E. coli and the resulting colonies were screened by colony hybridization to identify those that contained the dextranase coding region. From this screen, plasmid pJW111 was selected (FIG. 8). DNA sequencing of the insert in pJW111 determined that this was the dextranase gene and that the sequence was identical to that of the dextranase gene in pToC343.

Transformation of Fusarium venenatum

The plasmid pJW111 was introduced into a morphological mutant of Fusarium A3/5 (ATCC 20334), designated CC1-3, as follows:

Conidia were generated by growth of strain ATTC 20334 CC1-3 in sporulation medium at 28° C., 150 rpm for 2–4 days. Conidia were filtered through Miracloth, concentrated by centrifugation and re-suspended in sterile water. 50 ml of YPG medium was inoculated with $10^8$ conidia, and incubated for 14 hours at 24° C., 150 rpm. The resulting hyphae were resuspended in 20 ml of NOVOZYM 234 solution (2.5 mg/ml in 1.0 M $MgSO_4$) and digested for 15–45 minutes at 28° C. at 80 rpm. 30 ml of STC were added and protoplasts were pelleted at 1500 rpm (Sorvall RT 6000 centrifuge) for 10 minutes. STC wash steps were repeated twice. Protoplasts were suspended in STC:SPTC:DMSO (8:2:0.1) at a concentration of approximately $5 \times 10^7$ protoplasts per ml.

Plasmid DNA (2–20 mg) was added to 200 ml protoplasts and incubated 30 minutes on ice. Two ml SPTC were added slowly, followed by a 20 minute incubation at room temperature. 50 ml melted overlay (1×Vogel's salts, 25 mM $NaNO_3$, 0.8M sucrose, 1% low melt agarose) at 40° C. were added to the transformation reaction. Samples were mixed by inversion and split between two empty 150 mm petri dishes. After 24 hours 25 ml overlay plus 10 mg/ml Basta were added to each plate. Plates were incubated at room temperature.

Expression of Dextranase Activity 16 transformants were transferred to Vogel's/Basta and grown 7 days at room temperature. 20 ml M400Da medium in a 125 ml flask were inoculated with a 1 $cm^2$ piece of mycelia from the Vogel's/Basta plate. Cultures were incubated 7 days at 30° C., 150 rpm. Culture samples were centrifuged and the supernatants were assayed for dextranase (as described above). The best producing transformants were selected by dextranase activity assays and SDS/PAGE analysis. The dextranase band ran at approximately 60 kD on a 10–27% gradient tris-glycine gel.

N-terminal sequencing revealed that the dextranase expressed in F. venenatum was 100% correctly processed to Asn-Gln-Ala-Leu-, in contrast to the dextranase produced by A. oryzae, of which 40% was incorrectly processed to yield the N-terminal sequence Asp-Gln-Gln-Asn-Gln-Ala-Leu-.

We claim:

1. A DNA construct comprising a DNA sequence encoding an enzyme exhibiting dextranase activity, which DNA sequence comprises
   a) the dextranase encoding part of the DNA sequence of SEQ ID NO:1, and/or the DNA sequence obtainable from *E. coli* DSM 10706, or
   b) an analogue of the DNA sequence defined in a), which
      i) is 80% homologous with the DNA sequence of SEQ ID NO:1 and/or the DNA sequence obtainable from *E. coli* DSM 10706, or
      ii) encodes a polypeptide which is at least 80% homologous with the polypeptide encoded by the DNA sequence of SEQ ID NO:1 and/or the DNA sequence obtainable from *E. coli* DSM.

2. The DNA construct of claim 1, wherein the DNA sequence is obtained from a fungal microorganism.

3. The DNA construct of claim 2, wherein the fungal microorganism is a filamentous fungus or a yeast.

4. The DNA construct of claim 3, wherein the filamentous fungus is a strain of Paecilomyces or Penicillium.

5. The DNA construct of claim 4, wherein the strain is *Paecilomyces lilacinus*.

6. The DNA construct of claim 4, wherein the Penicillium strain is *Penicillium lilacinum* or *Penicillium minioluteum*.

7. A recombinant expression vector comprising the DNA construct of claim 1.

8. A cell comprising the recombinant expression vector of claim 7.

9. The cell of claim 8, which is a filamentous fungus.

10. The cell of claim 9, wherein the cell belongs to a strain within the genus Aspergillus Fusarium, Pencillium, or Paecilomyces.

11. The cell of claim 10, wherein the cell belongs to one of strain *Aspergillus niger, Aspergillus oryzae, Fusarium oxysporium, Fusarium graminearum, Fusarium sulphureum, Fusarium cerealis, Fusarium venenatum, Penicillium lilacinum, Penicillium minioluteum,* or *Paecilomyces lilacinus*.

12. A method for producing a recombinant enzyme exhibiting dextranase activity, which method comprises cultivating a host cell according to claim 8 in suitable culture medium under conditions permitting the expression of the DNA construct, and recovering the enzyme from the culture.

* * * * *

SEQUENCE LISTING

<160> NUMBER OF SEQ ID NOS: 26

<210> SEQ ID NO 1
<211> LENGTH: 2993
<212> TYPE: DNA
<213> ORGANISM: P. lilacinus
<220> FEATURE:
<221> NAME/KEY: CDS
<222> LOCATION: (875)...(2701)
<221> NAME/KEY: sig_peptide
<222> LOCATION: (875)...(958)
<221> NAME/KEY: mat_peptide
<222> LOCATION: (959)...(2701)

<400> SEQUENCE: 1

```
gacgaccatg acaggtgtcg cacaacagga acaatcagga ccctgatacg gccataaggt      60
gaaacacccc cttgatgaca acgggaagaa acagctggtc cgtatgttct agacaattca     120
aagacacatc ttcccctccc tgtccatgac actgtggtag gacgatgaca ccgatgcatg     180
atcatgaaag gacaatgaac atgggcgatc gatttagctg acatgaagtg tagcgaagac     240
aagtgcctcc gtgtttcgta gatcgagacc agagtggtgg caattgctcc ggctccaacc     300
cgatccagag atgggccgag tataactgat atgcgcccgc tttcgttaga ctgcgcatgg     360
agctgtggca catcgtcgtc cagaccaagg aagactagca atggtttggc cgctgtgtga     420
gccacgttcg ttttacatcc aactgccgcc ggccccccgt ggggtaacaa ggcggaggcg     480
tggggtaacc gggcggttcc cgttctgagt aatacgcctt ctgattgtgc caatctggag     540
cggtggtcgc tgcaggggga tggcccttct aacttctttc ttttaagctt atgaaactag     600
gccaggtggt ggctgtggca agtctcaaca gcgccataga ttgaatcaga catggacccc     660
ccgcaacatg tgtcccgccc cagaactcct gcgtcttcgg tcctctcccg ggaagagagt     720
gcgccgtcac caaggctata aatacttggg gtatgttagc atagtctcga aatgatatcc     780
catttcaatc tttactggtc catctctaaa ggcatacaca cagtgaggct gattttcggc     840
cattgtcctg tacacttacc tgtcaagcgg catc atg cgt tgg cct ggt aat ttt     895
                                   Met Arg Trp Pro Gly Asn Phe
                                                          -25 ctc act ctc gcg acg gcg ctg caa gct gct ggg aac ctc gcc gca agc      943
Leu Thr Leu Ala Thr Ala Leu Gln Ala Ala Gly Asn Leu Ala Ala Ser
    -20              -15                  -10 gtc cat cac agg tgt gat cag cag aat caa gcg cta cac aca tgg tgg      991
Val His His Arg Cys Asp Gln Gln Asn Gln Ala Leu His Thr Trp Trp
 -5                  1               5                  10 cac gaa aag tct gct gtc aac gac gcg ggg gct gtc gca gca gat gaa     1039
His Glu Lys Ser Ala Val Asn Asp Ala Gly Ala Val Ala Ala Asp Glu
             15                  20                  25 gtt cgc caa tcg cgc aag tac gat gtc tct gtg tcc gtt cgc gaa gaa     1087
Val Arg Gln Ser Arg Lys Tyr Asp Val Ser Val Ser Val Arg Glu Glu
         30                  35                  40 tcc aaa ttc cgg gac tcg ttt gtc tac gag acc atc ccg cgg aac ggc     1135
Ser Lys Phe Arg Asp Ser Phe Val Tyr Glu Thr Ile Pro Arg Asn Gly
     45                  50                  55 aac ggc aag atg tac gac ccg gcc aat cct ggt cag gaa tac aac ctg     1183
Asn Gly Lys Met Tyr Asp Pro Ala Asn Pro Gly Gln Glu Tyr Asn Leu
 60                  65                  70                  75 gcg gac ggg gat ggc atc acc gtc gaa gag gac gca aag atc aac atg     1231
Ala Asp Gly Asp Gly Ile Thr Val Glu Glu Asp Ala Lys Ile Asn Met
                 80                  85                  90 gct tgg acg cag ttt caa tac gcc aaa gat gtt gaa gtt cgc atc acc     1279
```

| | | | | | | | | | | | | |
|---|---|---|---|---|---|---|---|---|---|---|---|---|
|Ala|Trp|Thr|Gln|Phe|Gln|Tyr|Ala|Lys|Asp|Val|Glu|Val|Arg|Ile|Thr|
| | |  |95| | | |100| | | |105| | | | |

```
tcc aag gat ggt tct gca ctg ggg cca act agc aac gtt gtc atc cgc    1327
Ser Lys Asp Gly Ser Ala Leu Gly Pro Thr Ser Asn Val Val Ile Arg
        110                 115                 120 ccc tcg gat atc agg tac gac atc aga agc cca gac agc agc act gtt    1375
Pro Ser Asp Ile Arg Tyr Asp Ile Arg Ser Pro Asp Ser Ser Thr Val
125                 130                 135 ata atc cag gtt cca tac gac ctg agg ggc cga cga ttc tcc gtc gag    1423
Ile Ile Gln Val Pro Tyr Asp Leu Arg Gly Arg Arg Phe Ser Val Glu
140                 145                 150                 155 ttc caa aac gac tta tac gcc tac cgc tcg aac ggc aaa tca tat gtc    1471
Phe Gln Asn Asp Leu Tyr Ala Tyr Arg Ser Asn Gly Lys Ser Tyr Val
                160                 165                 170 aat gac ggc ggc gtt ctc gtg agc gag gaa ccg cgc aat gcg ctg ctt    1519
Asn Asp Gly Gly Val Leu Val Ser Glu Glu Pro Arg Asn Ala Leu Leu
            175                 180                 185 atc ttc gcc agt cca ttc att ccc cag gaa ctc atc ccg tcc aag aca    1567
Ile Phe Ala Ser Pro Phe Ile Pro Gln Glu Leu Ile Pro Ser Lys Thr
        190                 195                 200 tca ggc gat acg caa gtc ctc aag ccg ggc aag atc acc gac agc acc    1615
Ser Gly Asp Thr Gln Val Leu Lys Pro Gly Lys Ile Thr Asp Ser Thr
205                 210                 215 att ggc gcg aag ccg aca ctc tac ttt gag gca ggc acc tac tgg gta    1663
Ile Gly Ala Lys Pro Thr Leu Tyr Phe Glu Ala Gly Thr Tyr Trp Val
220                 225                 230                 235 gag aaa gac ggc cgc ctc ggt aaa agt cac atc aag ctg aac gcc aac    1711
Glu Lys Asp Gly Arg Leu Gly Lys Ser His Ile Lys Leu Asn Ala Asn
                240                 245                 250 acg cac tac gtc tac ttc gag cca gga act tat atc aaa ggc gcc ttt    1759
Thr His Tyr Val Tyr Phe Glu Pro Gly Thr Tyr Ile Lys Gly Ala Phe
            255                 260                 265 gag tac acc act tcg aag aat gac ttt tat acc gtc gga cat gga gta    1807
Glu Tyr Thr Thr Ser Lys Asn Asp Phe Tyr Thr Val Gly His Gly Val
        270                 275                 280 gtc tcg ggc gaa aat tac gca tac atg gca aac act gcc aag aac tat    1855
Val Ser Gly Glu Asn Tyr Ala Tyr Met Ala Asn Thr Ala Lys Asn Tyr
285                 290                 295 gtt gcg gaa aag agt gac cgg acc agt ctt agg atc ttt tcg cac cag    1903
Val Ala Glu Lys Ser Asp Arg Thr Ser Leu Arg Ile Phe Ser His Gln
300                 305                 310                 315 gca gtt tcg gac agc cag ata tgg cat tgc att gga cct acc ctt aat    1951
Ala Val Ser Asp Ser Gln Ile Trp His Cys Ile Gly Pro Thr Leu Asn
                320                 325                 330 gca ccg ccc ttt aat acc gtg gac ctg ttt cca aag aac cag acg cca    1999
Ala Pro Pro Phe Asn Thr Val Asp Leu Phe Pro Lys Asn Gln Thr Pro
            335                 340                 345 aac gag gaa gac aac aag gtg cgg aac gac atc tct gac tac aaa cag    2047
Asn Glu Glu Asp Asn Lys Val Arg Asn Asp Ile Ser Asp Tyr Lys Gln
        350                 355                 360 gtc ggc gcg ttc tac ttc cag act gat ggg ccg caa ata tac tct gga    2095
Val Gly Ala Phe Tyr Phe Gln Thr Asp Gly Pro Gln Ile Tyr Ser Gly
365                 370                 375 acc gtc aag gac tgc ttc tgg cat gtt aat gac gac gct atc aag ttg    2143
Thr Val Lys Asp Cys Phe Trp His Val Asn Asp Asp Ala Ile Lys Leu
380                 385                 390                 395 tac cac tcg gac gcg aag gtc gaa cgg gtg acc atc tgg aag tgt cac    2191
Tyr His Ser Asp Ala Lys Val Glu Arg Val Thr Ile Trp Lys Cys His
                400                 405                 410
```

```
aac gac ccc gtt atc caa atg ggc tgg aaa cca cgt gga gtc tct gga        2239
Asn Asp Pro Val Ile Gln Met Gly Trp Lys Pro Arg Gly Val Ser Gly
            415                 420                 425 act acc att tct gaa ctc aag gtc atc cac act cga tgg ttt aag agc        2287
Thr Thr Ile Ser Glu Leu Lys Val Ile His Thr Arg Trp Phe Lys Ser
        430                 435                 440 gag acg gtt gtt cct tcc gcc att att gga gcc tca ccc tac tac ggc        2335
Glu Thr Val Val Pro Ser Ala Ile Ile Gly Ala Ser Pro Tyr Tyr Gly
    445                 450                 455 gac cca aag att gtg gat gcg tct agg aca atg agc gtt cga att tct        2383
Asp Pro Lys Ile Val Asp Ala Ser Arg Thr Met Ser Val Arg Ile Ser
460                 465                 470                 475 gac gtg acc tgc gaa ggt cgt tgc cct gcg ctc ctt cgg att ggt ccg        2431
Asp Val Thr Cys Glu Gly Arg Cys Pro Ala Leu Leu Arg Ile Gly Pro
                480                 485                 490 ctc cag aat tat gac atg acc att gag aac gtg aaa ttc gat gaa ctt        2479
Leu Gln Asn Tyr Asp Met Thr Ile Glu Asn Val Lys Phe Asp Glu Leu
            495                 500                 505 ttg agg gat gac aac gtc aag cta gga cag agt ctg gtt ggt atg agg        2527
Leu Arg Asp Asp Asn Val Lys Leu Gly Gln Ser Leu Val Gly Met Arg
        510                 515                 520 atc agc gac caa gag gac gcc tac ata ccc ggc caa gaa aag ctc aag        2575
Ile Ser Asp Gln Glu Asp Ala Tyr Ile Pro Gly Gln Glu Lys Leu Lys
    525                 530                 535 cta ggg ata cat atc aag aat tgg cag att ggg ggc aac aga gtg gat        2623
Leu Gly Ile His Ile Lys Asn Trp Gln Ile Gly Gly Asn Arg Val Asp
540                 545                 550                 555 gga tca aac tgg caa gtc aac caa ctt ggg cag ttg aac atc cac ccc        2671
Gly Ser Asn Trp Gln Val Asn Gln Leu Gly Gln Leu Asn Ile His Pro
                560                 565                 570 gat tat tgg ggt gac tgg agc att gaa tga ggcaggctac cagaggatac          2721
Asp Tyr Trp Gly Asp Trp Ser Ile Glu
            575                 580 gtgtgtttcc gtgttggcgc acttccaaac ccatcacgcc gactgtttca attcttcgca      2781
tccagaagga tgctgcggcg tctgccgcaa tctgtatgtc ctacttcaat ggagaaatga      2841
ttatcgaaaa accagacctc accaaagaaa gtgcacgtgg ttaactaggg acatgagatg      2901
cccgacactg tagactctgc tcatcaagat aatccttctt gcacagcgct gataacgtga      2961
tggcgcccag tacgtgtagg ggcatccgag tc                                    2993

<210> SEQ ID NO 2
<211> LENGTH: 608
<212> TYPE: PRT
<213> ORGANISM: P. lilacinus
<220> FEATURE:
<221> NAME/KEY: SIGNAL
<222> LOCATION: (1)...(28)

<400> SEQUENCE: 2

Met Arg Trp Pro Gly Asn Phe Leu Thr Leu Ala Thr Ala Leu Gln Ala
            -25                 -20                 -15

Ala Gly Asn Leu Ala Ala Ser Val His His Arg Cys Asp Gln Gln Asn
        -10                  -5                   1

Gln Ala Leu His Thr Trp Trp His Glu Lys Ser Ala Val Asn Asp Ala
 5                  10                  15                  20

Gly Ala Val Ala Ala Asp Glu Val Arg Gln Ser Arg Lys Tyr Asp Val
                25                  30                  35

Ser Val Ser Val Arg Glu Glu Ser Lys Phe Arg Asp Ser Phe Val Tyr
            40                  45                  50
```

-continued

Glu Thr Ile Pro Arg Asn Gly Asn Gly Lys Met Tyr Asp Pro Ala Asn
         55                  60                  65

Pro Gly Gln Glu Tyr Asn Leu Ala Asp Gly Asp Gly Ile Thr Val Glu
     70                  75                  80

Glu Asp Ala Lys Ile Asn Met Ala Trp Thr Gln Phe Gln Tyr Ala Lys
 85                  90                  95                 100

Asp Val Glu Val Arg Ile Thr Ser Lys Asp Gly Ser Ala Leu Gly Pro
                 105                 110                 115

Thr Ser Asn Val Val Ile Arg Pro Ser Asp Ile Arg Tyr Asp Ile Arg
             120                 125                 130

Ser Pro Asp Ser Ser Thr Val Ile Ile Gln Val Pro Tyr Asp Leu Arg
             135                 140                 145

Gly Arg Arg Phe Ser Val Glu Phe Gln Asn Asp Leu Tyr Ala Tyr Arg
         150                 155                 160

Ser Asn Gly Lys Ser Tyr Val Asn Asp Gly Gly Val Leu Val Ser Glu
165                 170                 175                 180

Glu Pro Arg Asn Ala Leu Leu Ile Phe Ala Ser Pro Phe Ile Pro Gln
                 185                 190                 195

Glu Leu Ile Pro Ser Lys Thr Ser Gly Asp Thr Gln Val Leu Lys Pro
                 200                 205                 210

Gly Lys Ile Thr Asp Ser Thr Ile Gly Ala Lys Pro Thr Leu Tyr Phe
             215                 220                 225

Glu Ala Gly Thr Tyr Trp Val Glu Lys Asp Gly Arg Leu Gly Lys Ser
         230                 235                 240

His Ile Lys Leu Asn Ala Asn Thr His Tyr Val Tyr Phe Glu Pro Gly
245                 250                 255                 260

Thr Tyr Ile Lys Gly Ala Phe Glu Tyr Thr Thr Ser Lys Asn Asp Phe
                 265                 270                 275

Tyr Thr Val Gly His Gly Val Val Ser Gly Glu Asn Tyr Ala Tyr Met
             280                 285                 290

Ala Asn Thr Ala Lys Asn Tyr Val Ala Glu Lys Ser Asp Arg Thr Ser
         295                 300                 305

Leu Arg Ile Phe Ser His Gln Ala Val Ser Asp Ser Gln Ile Trp His
     310                 315                 320

Cys Ile Gly Pro Thr Leu Asn Ala Pro Pro Phe Asn Thr Val Asp Leu
325                 330                 335                 340

Phe Pro Lys Asn Gln Thr Pro Asn Glu Glu Asp Asn Lys Val Arg Asn
                 345                 350                 355

Asp Ile Ser Asp Tyr Lys Gln Val Gly Ala Phe Tyr Phe Gln Thr Asp
             360                 365                 370

Gly Pro Gln Ile Tyr Ser Gly Thr Val Lys Asp Cys Phe Trp His Val
         375                 380                 385

Asn Asp Asp Ala Ile Lys Leu Tyr His Ser Asp Ala Lys Val Glu Arg
     390                 395                 400

Val Thr Ile Trp Lys Cys His Asn Asp Pro Val Ile Gln Met Gly Trp
405                 410                 415                 420

Lys Pro Arg Gly Val Ser Gly Thr Thr Ile Ser Glu Leu Lys Val Ile
                 425                 430                 435

His Thr Arg Trp Phe Lys Ser Glu Thr Val Val Pro Ser Ala Ile Ile
             440                 445                 450

Gly Ala Ser Pro Tyr Tyr Gly Asp Pro Lys Ile Val Asp Ala Ser Arg
         455                 460                 465

```
Thr Met Ser Val Arg Ile Ser Asp Val Thr Cys Glu Gly Arg Cys Pro
    470                 475                 480
Ala Leu Leu Arg Ile Gly Pro Leu Gln Asn Tyr Asp Met Thr Ile Glu
485                 490                 495                 500
Asn Val Lys Phe Asp Glu Leu Leu Arg Asp Asn Val Lys Leu Gly
                505                 510                 515
Gln Ser Leu Val Gly Met Arg Ile Ser Asp Gln Glu Asp Ala Tyr Ile
            520                 525                 530
Pro Gly Gln Glu Lys Leu Lys Leu Gly Ile His Ile Lys Asn Trp Gln
            535                 540                 545
Ile Gly Gly Asn Arg Val Asp Gly Ser Asn Trp Gln Val Asn Gln Leu
    550                 555                 560
Gly Gln Leu Asn Ile His Pro Asp Tyr Trp Gly Asp Trp Ser Ile Glu
565                 570                 575                 580

<210> SEQ ID NO 3
<211> LENGTH: 15
<212> TYPE: PRT
<213> ORGANISM: P. lilacinus

<400> SEQUENCE: 3

Asp Gln Gln Asn Gln Ala Leu His Thr Trp Trp His Glu Lys Ser
1               5                   10                  15

<210> SEQ ID NO 4
<211> LENGTH: 28
<212> TYPE: PRT
<213> ORGANISM: P. lilacinus

<400> SEQUENCE: 4

Ser Tyr Val Asn Asp Gly Gly Val Leu Val Ser Glu Glu Pro Arg Asn
1               5                   10                  15
Ala Leu Leu Ile Phe Ala Ser Pro Phe Ile Pro Gln
            20                  25

<210> SEQ ID NO 5
<211> LENGTH: 23
<212> TYPE: PRT
<213> ORGANISM: P. lilacinus
<220> FEATURE:
<221> NAME/KEY: PEPTIDE
<222> LOCATION: (0)...(0)
<223> OTHER INFORMATION: Xaa = unknown

<400> SEQUENCE: 5

Ser Asp Arg Thr Ser Leu Arg Ile Phe Ser His Gln Ala Val Ser Asp
1               5                   10                  15
Ser Gln Ile Trp His Xaa Ile
            20

<210> SEQ ID NO 6
<211> LENGTH: 24
<212> TYPE: PRT
<213> ORGANISM: P. lilacinus

<400> SEQUENCE: 6

Asn Asp Phe Tyr Thr Val Gly His Gly Val Val Ser Gly Glu Asn Tyr
1               5                   10                  15
Ala Tyr Met Ala Asn Thr Ala Lys
            20
```

-continued

```
<210> SEQ ID NO 7
<211> LENGTH: 12
<212> TYPE: PRT
<213> ORGANISM: P. lilacinus

<400> SEQUENCE: 7

Ile Asn Ala Ala Trp Thr Gln Phe Gln Tyr Ala Lys
 1               5                  10

<210> SEQ ID NO 8
<211> LENGTH: 26
<212> TYPE: PRT
<213> ORGANISM: P. lilacinus

<400> SEQUENCE: 8

Asp Gly Ser Ala Leu Gly Pro Thr Ser Asn Val Val Ile Arg Pro Ser
 1               5                  10                  15

Asp Ile Arg Tyr Asp Ile Ser Ser Pro Asp
             20                  25

<210> SEQ ID NO 9
<211> LENGTH: 18
<212> TYPE: PRT
<213> ORGANISM: P. lilacinus

<400> SEQUENCE: 9

Asn Trp Gln Ile Gly Gly Asn Arg Val Asp Gly Ser Asn Trp Gln Val
 1               5                  10                  15

Asn Gln

<210> SEQ ID NO 10
<211> LENGTH: 19
<212> TYPE: PRT
<213> ORGANISM: P. lilacinus

<400> SEQUENCE: 10

Ser Glu Thr Val Val Pro Ser Ala Ile Ile Gly Ala Ser Pro Tyr Tyr
 1               5                  10                  15

Gly Asp Pro

<210> SEQ ID NO 11
<211> LENGTH: 17
<212> TYPE: PRT
<213> ORGANISM: P. lilacinus

<400> SEQUENCE: 11

Leu Asx Ala Asx Thr His Tyr Val Tyr Phe Glu Pro Gly Thr Tyr Ile
 1               5                  10                  15

Lys

<210> SEQ ID NO 12
<211> LENGTH: 7
<212> TYPE: PRT
<213> ORGANISM: P. lilacinus

<400> SEQUENCE: 12

Val Ile His Thr Arg Trp Phe
 1               5

<210> SEQ ID NO 13
<211> LENGTH: 19
<212> TYPE: PRT
<213> ORGANISM: P. lilacinus
```

-continued

```
<400> SEQUENCE: 13

Ser Ala Val Asn Asp Ala Gly Ala Val Ala Ala Asp Glu Val Arg Gln
1               5                   10                  15

Ser Ala Lys

<210> SEQ ID NO 14
<211> LENGTH: 12
<212> TYPE: PRT
<213> ORGANISM: P. lilacinus
<220> FEATURE:
<221> NAME/KEY: PEPTIDE
<222> LOCATION: (0)...(0)
<223> OTHER INFORMATION: Xaa = unknown

<400> SEQUENCE: 14

Xaa His Asn Asp Pro Val Ile Gln Met Gly Xaa Lys
1               5                   10

<210> SEQ ID NO 15
<211> LENGTH: 20
<212> TYPE: DNA
<213> ORGANISM: P. lilacinus
<220> FEATURE:
<221> NAME/KEY: misc_feature
<222> LOCATION: (0)...(0)
<223> OTHER INFORMATION: n = t, c, g, a

<400> SEQUENCE: 15
garaaytayg cntayatggc                                              20

<210> SEQ ID NO 16
<211> LENGTH: 20
<212> TYPE: DNA
<213> ORGANISM: P. lilacinus
<220> FEATURE:
<221> NAME/KEY: misc_feature
<222> LOCATION: (0)...(0)
<223> OTHER INFORMATION: n = g, a, t, c

<400> SEQUENCE: 16
gccatrtang crtarttytc                                              20

<210> SEQ ID NO 17
<211> LENGTH: 20
<212> TYPE: DNA
<213> ORGANISM: P. lilacinus
<220> FEATURE:
<221> NAME/KEY: misc_feature
<222> LOCATION: (0)...(0)
<223> OTHER INFORMATION: n = a, g, t, c

<400> SEQUENCE: 17
tggacncart tycartaygc                                              20

<210> SEQ ID NO 18
<211> LENGTH: 19
<212> TYPE: DNA
<213> ORGANISM: P. lilacinus
<220> FEATURE:
<221> NAME/KEY: misc_feature
<222> LOCATION: (0)...(0)
<223> OTHER INFORMATION: n = a, g, t, c

<400> SEQUENCE: 18
gcrtaytgra aytgngtcc                                               19
```

<210> SEQ ID NO 19
<211> LENGTH: 17
<212> TYPE: DNA
<213> ORGANISM: P. lilacinus
<220> FEATURE:
<221> NAME/KEY: misc_feature
<222> LOCATION: (0)...(0)
<223> OTHER INFORMATION: n = a, g, t, c

<400> SEQUENCE: 19
aaytggcara thggngg                                                 17

<210> SEQ ID NO 20
<211> LENGTH: 17
<212> TYPE: DNA
<213> ORGANISM: P. lilacinus
<220> FEATURE:
<221> NAME/KEY: misc_feature
<222> LOCATION: (0)...(0)
<223> OTHER INFORMATION: n = a, g, t, c

<400> SEQUENCE: 20
ccnccdtayt gccartt                                                 17

<210> SEQ ID NO 21
<211> LENGTH: 21
<212> TYPE: DNA
<213> ORGANISM: Aspergillus nidulans

<400> SEQUENCE: 21
agaaatcggg tatcctttca g                                            21

<210> SEQ ID NO 22
<211> LENGTH: 105
<212> TYPE: DNA
<213> ORGANISM: Aspergillus nidulans

<400> SEQUENCE: 22
gctcctcatg gtggatcccc agttgtgtat atagaggatt gaggaaggaa gagaagtgtg    60
gatagaggta aattgagttg gaaactccaa gcatggcatc cttgc                  105

<210> SEQ ID NO 23
<211> LENGTH: 34
<212> TYPE: DNA
<213> ORGANISM: P. lilacinus

<400> SEQUENCE: 23
cgcggatcca ccatgcgttg gcctggtaat tttc                              34

<210> SEQ ID NO 24
<211> LENGTH: 29
<212> TYPE: DNA
<213> ORGANISM: P. lilacinus

<400> SEQUENCE: 24
ccgctcgagc ctgcctcatt caatgctcc                                    29

<210> SEQ ID NO 25
<211> LENGTH: 25
<212> TYPE: DNA
<213> ORGANISM: P. lilacinus

<400> SEQUENCE: 25
gcatttaaat atgcgttggc ctggt                                        25

```
<210> SEQ ID NO 26
<211> LENGTH: 28
<212> TYPE: DNA
<213> ORGANISM: P. lilacinus

<400> SEQUENCE: 26
cgttaattaa tcattcaatg ctccagtc                                            28
```